US012564675B1

(12) United States Patent
Dave et al.

(10) Patent No.: US 12,564,675 B1
(45) Date of Patent: Mar. 3, 2026

(54) AUTOPILOT DRUG-DELIVERY SYSTEM

(71) Applicant: MantaMedTech LLC, Newark, DE (US)

(72) Inventors: Raju S. Dave, Gaithersburg, MD (US); Xing Su, Santa Clara, CA (US); Narayanan Surendran, Princeton Junction, NJ (US); Michael A. Ross, McLean, VA (US); Himanshu Verma, McLean, VA (US); Kenta Alten, Los Altos Hills, CA (US)

(73) Assignee: Manta MedTech LLC

( * ) Notice: Subject to any disclaimer, the term of this patent is extended or adjusted under 35 U.S.C. 154(b) by 0 days.

(21) Appl. No.: 19/007,650

(22) Filed: Jan. 2, 2025

(51) Int. Cl.
　　*A61M 5/142* 　　(2006.01)
　　*G16H 20/17* 　　(2018.01)
　　*A61M 5/172* 　　(2006.01)

(52) U.S. Cl.
　　CPC ........ *A61M 5/14276* (2013.01); *G16H 20/17* (2018.01); *A61M 2005/1726* (2013.01); *A61M 2205/52* (2013.01)

(58) Field of Classification Search
　　None
　　See application file for complete search history.

(56) References Cited

U.S. PATENT DOCUMENTS

| | | | | |
|---|---|---|---|---|
| 6,931,327 | B2 * | 8/2005 | Goode, Jr. | ........... A61B 5/1495 702/22 |
| 8,285,328 | B2 * | 10/2012 | Caffey | .............. A61M 5/14526 417/213 |

| | | | | |
|---|---|---|---|---|
| 11,000,213 | B2 | 5/2021 | Kamath et al. | |
| 11,367,519 | B1 | 6/2022 | Heldman et al. | |
| 12,029,559 | B2 | 7/2024 | Rader et al. | |
| 12,062,423 | B2 * | 8/2024 | Bakos | ................. A61M 15/009 |
| 12,102,445 | B2 * | 10/2024 | Shelton, IV | ........ A61M 15/009 |
| 2011/0184342 | A1 | 7/2011 | Pesach et al. | |
| 2018/0174675 | A1 * | 6/2018 | Roy | ....................... G16H 10/60 |
| 2019/0175079 | A1 * | 6/2019 | Nishida | .............. G01N 27/3274 |
| 2020/0245925 | A1 | 8/2020 | Inwald et al. | |
| 2021/0319872 | A1 | 10/2021 | Valentine | |
| 2021/0345954 | A1 * | 11/2021 | Shelton, IV | ......... A61B 5/4266 |
| 2021/0350897 | A1 * | 11/2021 | Shelton, IV | .......... A61M 5/326 |
| 2022/0361758 | A1 | 11/2022 | Albertini et al. | |

(Continued)

OTHER PUBLICATIONS

Search report and Written opinion issued for PCT/US2025/010030, mailed on Jul. 9, 2025, 20 pages.

(Continued)

*Primary Examiner* — Manuel A Mendez
(74) *Attorney, Agent, or Firm* — Raj S. Dave; Dave Law Group LLC

(57) ABSTRACT

An embodiment relates to systems and methods to deliver medications precisely within body of a subject as prescribed and tailored to individual needs. The system comprises a miniaturized implantable drug delivery device that dispenses drugs subcutaneously with controlled precision; a stable drug formulation that remains effective at body temperature; a biosensor that continuously monitors at least one of a drug level and health markers; and an analytics platform that analyses data to optimize drug delivery in real-time, ensuring highly personalized and effective patient care.

20 Claims, 16 Drawing Sheets

IMPLANTABLE DEVICE (OUTSIDE VIEW)

(56) References Cited

U.S. PATENT DOCUMENTS

2023/0389856 A1    12/2023   Heasman et al.

OTHER PUBLICATIONS

Asheesh Divetia, "Custom Integrated Circuits Enabling Advancements in Implantable Drug Delivery Systems", ONdrugDelivery • Issue 168, 2005, 103-105.

Iwona Cicha et al., "Biosensor-Integrated Drug Delivery Systems as New Materials for Biomedical Applications", Biomolecules, Aug. 29, 2022;12(9):1198. doi: 10.3390/biom12091198.

David Yogev et al., "Current state of the art and future directions for implantable sensors in medical technology: Clinical needs and engineering challenges", APL Bioeng Sep. 27, 2023;7(3):031506. doi: 10.1063/5.0152290.

Jacob Anthony et al. "Feedback Control of Medication Delivery Device Using Machine Learning-Based Control Co-Design", Journal of Software Engineering and Applications, 2022, 15, 220-239 https://www.scirp.org/journal/jsea.

Giovanny Marquez et al., "Delivering biochemicals with precision using bioelectronic devices enhanced with feedback control", May 14, 2024, https://doi.org/10.1371/journal.pone.0298286.

* cited by examiner

IMPLANTABLE DEVICE (OUTSIDE VIEW)

600

START

[602] RECEIVING DATA FROM THE DEVICE
[602.1] GATHERING CLINICAL RECORDS
[602.2] ENSURING DATA QUALITY AND COMPLETENESS
[602.3] SELECTING RELEVANT FEATURES (PARAMETERS)

[604] PREPROCESSING DATA
[604.1] HANDLING MISSING DATA
[604.2] NORMALIZING OR SCALE FEATURES
[604.3] ENCODING CATEGORICAL VARIABLES

[606] SELECTING A MODEL
[606.1] CHOOSING AN APPROPRIATE MACHINE LEARNING ALGORITHM
[606.2] SPLITTING DATA INTO TRAINING AND TESTING SETS
[606.3] INITIALIZING MODEL WITH HYPERPARAMETERS

[608] TRAINING THE MODEL
[608.1] TRAINING THE MODEL ON THE TRAINING SET
[608.2] VALIDATING THE MODEL ON A SEPARATE VALIDATION SET
[608.3] ADJUSTING HYPERPARAMETERS IF NEEDED

[610] EVALUATING THE MODEL
[610.1] EVALUATING MODEL PERFORMANCE ON THE TESTING SET
[610.2] ASSESSING METRICS (e.g., MEAN ABSOLUTE ERROR)

[612] DEVELOPING/REFINING A DOSE-SELECTION ALGORITHM
[612.1] DEVELOPING ALGORITHM BASED ON MODEL PREDICTIONS
[612.2] CONSIDERING CLINICAL GUIDELINES AND CONSTRAINTS

[614] MODEL DEPLOYMENT
[614] MODEL DEPLOYMENING THE MODEL
[614.1] DEPLOYING MODEL IN A SUITABLE ENVIRONMENT
[614.2] INTEGRATING MODEL WITH CLINICAL SYSTEMS

[616] RECOMMENDING DOSE
[616.1] SENDING DOSING RECOMMENDATIONS TO PHYSICIANS
[616.2] ALLOWING PHYSICIAN FEEDBACK OR ADJUSTMENTS

[618] ADMINISTRING THE DOSE TO THE PATIENT
[618.1] ADMINISTERING PRESCRIBED DRUG DOSES TO PATIENTS
[618.2] MONITORING PATIENT RESPONSE AND ADVERSE EFFECTS

[620] FEEDBACK LOOP
[620.1] CONTINUOUSLY GATHERING NEW CLINICAL DATA
[620.2] RETRAINING THE MODEL PERIODICALLY

END

FIG. 6

START

[702] RECIVING CLINICAL RECORDS
[702.1] RECIVING DATA FROM A CLINICAL DATABASE
[702.2] RECEIVING PATIENT PROFILE

[704] TRAINING PREDICTIVE MODEL
[704.1] USING MACHINE LEARNING ON N CLINICAL RECORDS
[704.2] VALIDATING MODEL ON > X RECORDS
[704.3] EVALUATING MODEL'S MEAN ABSOLUTE PREDICTION ERROR

[706] DEVELOPING DOSE-SELECTION ALGORITHM
[706.1] USING CLINICAL GUIDELINES FOR ANEMIA TREATMENT
[706.2] SIMULATING DRUG DOSES ON THE PREDICTIVE MODEL
[706.3] SELECTING DOSE MOVING Hb TO THE TARGET INTERVAL
[706.4] SETTING VALUES FOR EXCESSIVE HB DECREASES OR INCREASES

[708] TRIGGERING ANEMIA CONTROL MODEL (ACM) CONDITION
[708.1] TRIGGERING ON NEW HB VALUE
[708.2] CHECKING PATIENT ELIGIBILITY

[710] IDENTIFYING ACM INELIGIBILITY CONDITION
[710.1] CHECKING TEMPORARILY INELIGIBLE CONDITIONS

[1012] CHECKING DATA REQUIREMENTS
[712.1] CHECKING CLINICAL DATA FOR THE PAST 90 DAYS
[712.2] CHECKING INFORMATION ON DRUGS ADMINISTERED

[714] RECIVING PATIENTS ASSESSMENT DATA
[712.1] RECEIVING INFORMATION ON PATIENTS DEEMED INELIGIBLE FOR
ESA THERAPY FROM A USER INTERFACE

[716] RECOMMENDING A DRUG DOSE
[716.1] PROVIDING DOSE RECOMMENDATIONS
[716.2] RECIVING EVALUATION VALIDITY DATA ON AN INDIVIDUAL BASIS
[716.2] RECEIVING EVALUATION VALIDITY DATA ON AN INDIVIDUAL BASIS
[716.3] EVALUATING WHETHER TO ACCEPT OR FORMULATE A DIFFERENT
DOSE

[718] INTEGRATING NEPHROCARE CLINICS DATABASE
[1018.1] SUGGESTING ALTERNATIVE DRUG
[718.1] SUGGESTING ALTERNATIVE DRUG
[718.2] CONVERTING SUGGESTIONS INTO PRESCRIPTIONS UPON
ACCEPTANCE
[718.3] RECIVING RESONS FROM PHYSICIANS FOR REJECTED SUGGESTIONS
718.3] RECEIVING RESONS FROM PHYSICIANS FOR REJECTED SUGGESTIONS

[720] UPDATING DATA TO ACM
[720.1] INTERFACING MODULE WITH THE CLINICAL DATABASE
[720.2] FEEDING UPDATED CLINICAL DATA TO THE MODEL

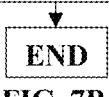

END

FIG. 7B

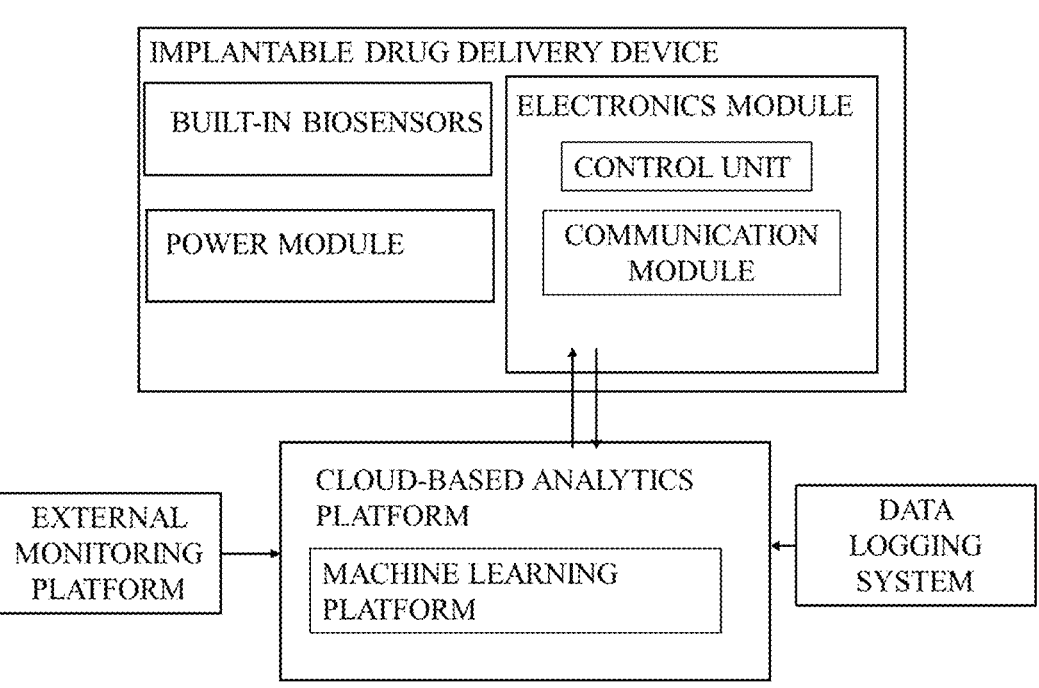

FIG. 8

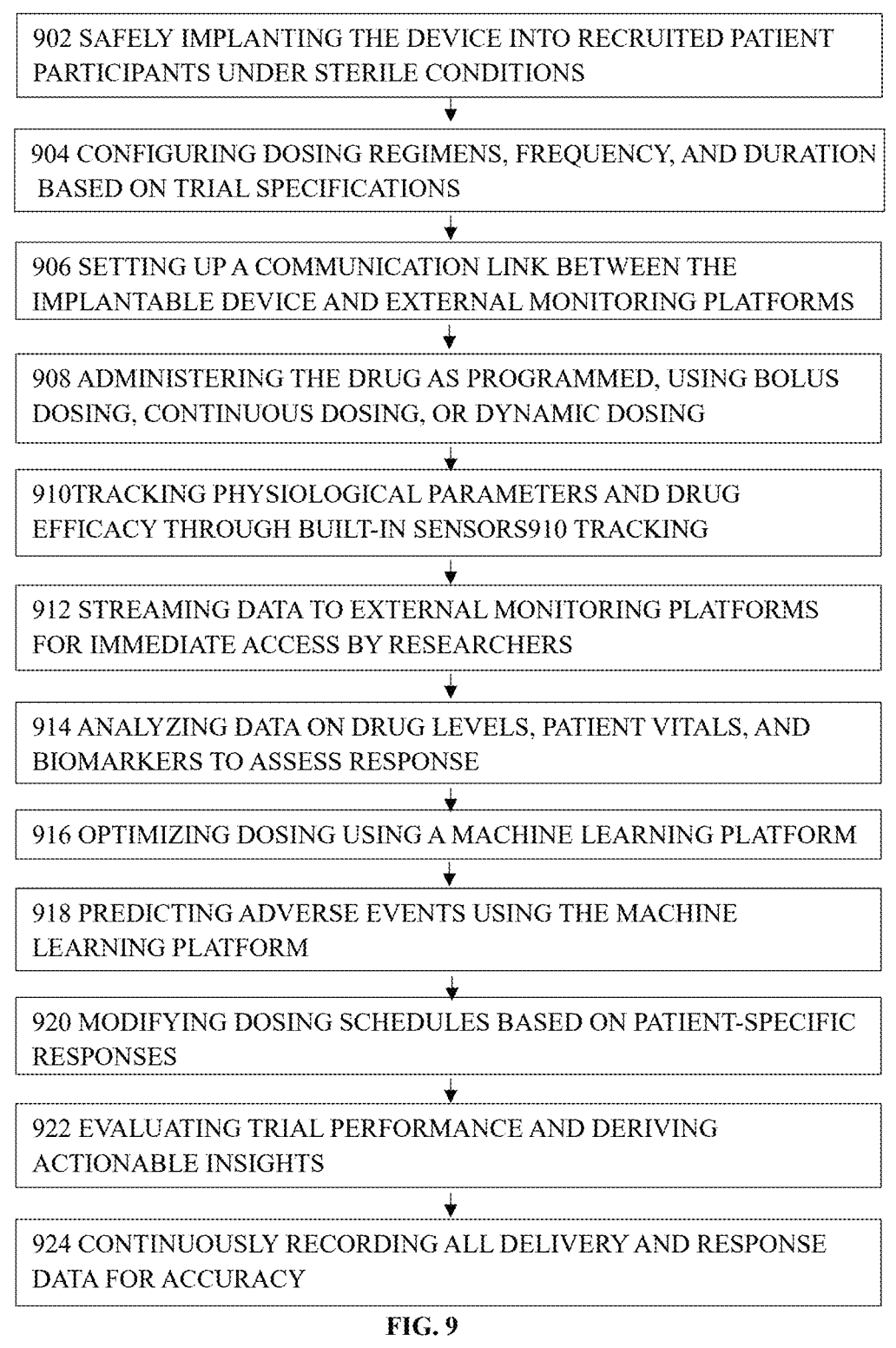

902 SAFELY IMPLANTING THE DEVICE INTO RECRUITED PATIENT PARTICIPANTS UNDER STERILE CONDITIONS

↓

904 CONFIGURING DOSING REGIMENS, FREQUENCY, AND DURATION BASED ON TRIAL SPECIFICATIONS

↓

906 SETTING UP A COMMUNICATION LINK BETWEEN THE IMPLANTABLE DEVICE AND EXTERNAL MONITORING PLATFORMS

↓

908 ADMINISTERING THE DRUG AS PROGRAMMED, USING BOLUS DOSING, CONTINUOUS DOSING, OR DYNAMIC DOSING

↓

910TRACKING PHYSIOLOGICAL PARAMETERS AND DRUG EFFICACY THROUGH BUILT-IN SENSORS910 TRACKING

↓

912 STREAMING DATA TO EXTERNAL MONITORING PLATFORMS FOR IMMEDIATE ACCESS BY RESEARCHERS

↓

914 ANALYZING DATA ON DRUG LEVELS, PATIENT VITALS, AND BIOMARKERS TO ASSESS RESPONSE

↓

916 OPTIMIZING DOSING USING A MACHINE LEARNING PLATFORM

↓

918 PREDICTING ADVERSE EVENTS USING THE MACHINE LEARNING PLATFORM

↓

920 MODIFYING DOSING SCHEDULES BASED ON PATIENT-SPECIFIC RESPONSES

↓

922 EVALUATING TRIAL PERFORMANCE AND DERIVING ACTIONABLE INSIGHTS

↓

924 CONTINUOUSLY RECORDING ALL DELIVERY AND RESPONSE DATA FOR ACCURACY

FIG. 9

| IDENTIFIING AN EXISTING DRUG WITH POTENTIAL FOR NEW THERAPEUTIC INDICATION/ OR A NEW PHYSICAL PROPERTY |
| REFORMULATING THE DRUG INTO A REPURPOSED DRUG FOR COMPATIBILITY WITH THE IMPLANTABLE DEVICE |
| IMPLANTING THE DEVICE COMPRISING THE REPURPOSED DRUG INTO A SUBJECT'S BODY |
| CONFIGURING A DOSING REGIME FOR THE REPURPOSED DRUG |
| ADMINSTRING THE REPURPOSED DRUG VIA THE IMPLANTED DEVICE INTO THE SUBJECTS'S BODY |
| REAL TIME MONITORING OF PHYSIOLOGICAL PARAMETERS AND BIOMARKERS RELEVANT TO THE REPURPOSED DRUGS EFFICACY |
| MEASURING LOCAL AND SYSTEMIC LEVELS OF THE REPURPOSED DRUG |
| TRANSMITTING DATA FROM THE IMPLANTABLE DEVICE TO AN EXTERNAL MONITORING PLATFORM |
| ANALYSING DATA TO ASSESS EFFICACY AND SAFETY OF THE REPURPOSED DRUG |
| ADAPTING THE DOSING REGIME BASED ON REAL TIME FEEDBACK FROM THE BIOSENSORS AND ANALYTICS |

FIG. 10

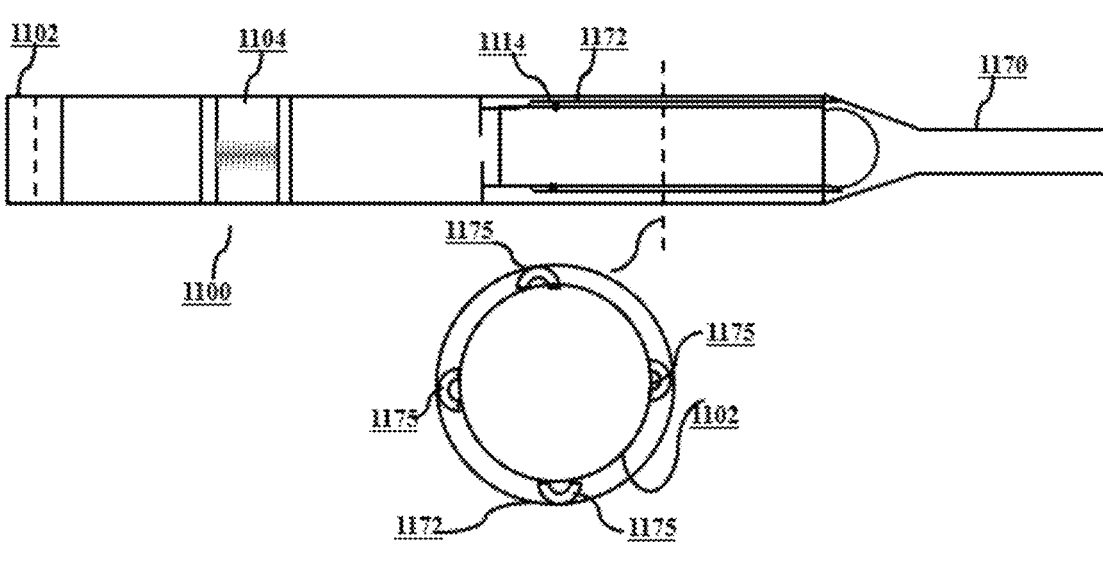

FIG. 11A

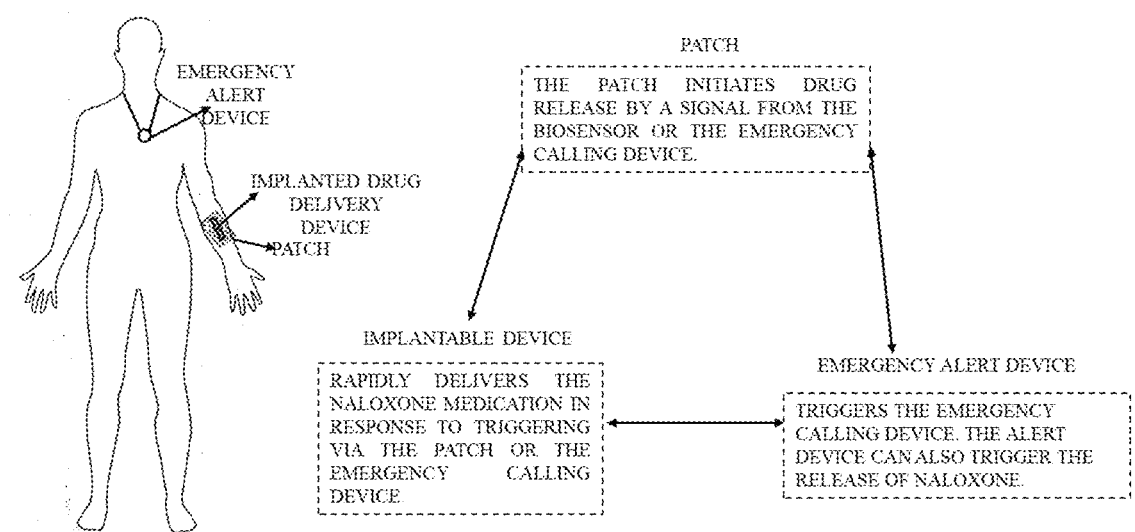

EMERGENCY ALERT DEVICE

IMPLANTED DRUG DELIVERY DEVICE

PATCH

PATCH

THE PATCH INITIATES DRUG RELEASE BY A SIGNAL FROM THE BIOSENSOR OR THE EMERGENCY CALLING DEVICE.

IMPLANTABLE DEVICE

RAPIDLY DELIVERS THE NALOXONE MEDICATION IN RESPONSE TO TRIGGERING VIA THE PATCH OR THE EMERGENCY CALLING DEVICE

EMERGENCY ALERT DEVICE

TRIGGERS THE EMERGENCY CALLING DEVICE. THE ALERT DEVICE CAN ALSO TRIGGER THE RELEASE OF NALOXONE.

1502 DATA COLLECTION USING AT LEAST ONE OF A WEARABLE DEVICE, PATCH OR DRUG DELIVERY DEVICE

1504 DATA PREPROCESSING

1506 FEATURE EXTRACTION FROM THE COLLECTED DATA

1508 MODEL DEVELOPMENT USING MACHINE LEARNING ALGORITHM

1510 SEVERITY CLASSIFICATION BASED ON EXTRACTED FEATURES AND HUMAN INPUT TO RE-DEVELOP, REFINE, AND TRAIN THE MODEL.

1512 MODEL EVALUATION

1514 MODEL DEPLOYMENT TO AT LEAST ONE OF THE WEARABLE DEVICE, THE PATCH, AND THE DRUG DELIVERY DEVICE

1516 DRUG DOSING VIA THE IMPLANTABLE DEVICE

1518 ALERT GENERATION VIA AT LEAST ONE OF THE WEARABLE DEVICE AND THE PATCH

FIG. 15

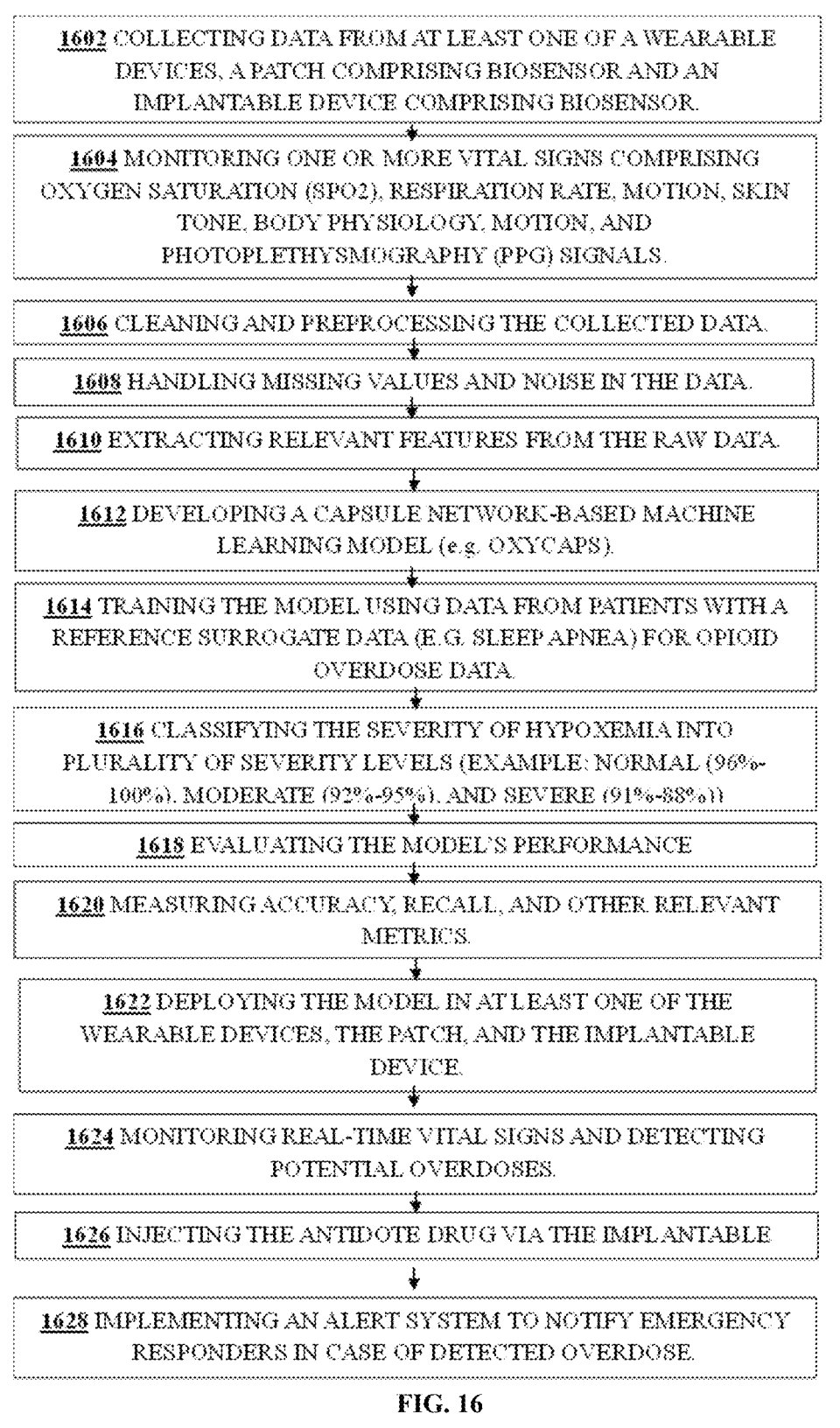

1602 COLLECTING DATA FROM AT LEAST ONE OF A WEARABLE DEVICES, A PATCH COMPRISING BIOSENSOR AND AN IMPLANTABLE DEVICE COMPRISING BIOSENSOR.

1604 MONITORING ONE OR MORE VITAL SIGNS COMPRISING OXYGEN SATURATION (SPO2), RESPIRATION RATE, MOTION, SKIN TONE, BODY PHYSIOLOGY, MOTION, AND PHOTOPLETHYSMOGRAPHY (PPG) SIGNALS.

1606 CLEANING AND PREPROCESSING THE COLLECTED DATA.

1608 HANDLING MISSING VALUES AND NOISE IN THE DATA.

1610 EXTRACTING RELEVANT FEATURES FROM THE RAW DATA.

1612 DEVELOPING A CAPSULE NETWORK-BASED MACHINE LEARNING MODEL (e.g. OXYCAPS).

1614 TRAINING THE MODEL USING DATA FROM PATIENTS WITH A REFERENCE SURROGATE DATA (E.G. SLEEP APNEA) FOR OPIOID OVERDOSE DATA.

1616 CLASSIFYING THE SEVERITY OF HYPOXEMIA INTO PLURALITY OF SEVERITY LEVELS (EXAMPLE: NORMAL (96%-100%), MODERATE (92%-95%), AND SEVERE (91%-88%))

1618 EVALUATING THE MODEL'S PERFORMANCE

1620 MEASURING ACCURACY, RECALL, AND OTHER RELEVANT METRICS.

1622 DEPLOYING THE MODEL IN AT LEAST ONE OF THE WEARABLE DEVICES, THE PATCH, AND THE IMPLANTABLE DEVICE.

1624 MONITORING REAL-TIME VITAL SIGNS AND DETECTING POTENTIAL OVERDOSES.

1626 INJECTING THE ANTIDOTE DRUG VIA THE IMPLANTABLE

1628 IMPLEMENTING AN ALERT SYSTEM TO NOTIFY EMERGENCY RESPONDERS IN CASE OF DETECTED OVERDOSE.

FIG. 16

AUTOPILOT DRUG-DELIVERY SYSTEM

CROSS REFERENCE TO RELATED APPLICATIONS

This application claims priority from the following applications shown in the Table below, which are incorporated by reference herein in its entirety.

| US Patent Application Nos. | Filing Date | Title of the Invention |
|---|---|---|
| 63617054 | 2 JAN. 2024 | PERSONALIZED DRUG DOSING |
| 63617057 | 2 JAN. 2024 | INNOVATIVE IMPLANTABLE DEVICE USING DOSING CONTROL TO PREVENT MEDICATION ERRORS |
| 63617754 | 4 JAN. 2024 | IMPLANTABLE DEVICE FOR PRECISION DOSING |
| 63566519 | 18 MAR. 2024 | IMPLANTABLE DRUG DELIVERY DEVICE |
| 63574330 | 4 APR. 2024 | INNOVATIVE IMPLANTABLE DEVICE USING DOSING CONTROL TO PREVENT MEDICATION ERRORS |
| 63661654 | 19 JUN. 2024 | DEVICE BASED TREATMENTS FOR SUBSTANCE USE DISORDERS |
| 18781451 | 23 JUL. 2024 | ARTIFICIAL INTELLIGENCE BASED IMPLANTABLE DRUG DELIVERY SYSTEM |
| 63689805 | 2 SEP. 2024 | IMPLANTABLE DEVICE FOR DRUG DELIVERY |
| 63707896 | 16 OCT. 2024 | DEVICE BASED TREATMENTS FOR SUBSTANCE USE DISORDERS |
| 63713149 | 29 OCT. 2024 | AUTOMATED OVERDOSE RESPONSE SYSTEM FOR ON-DEMAND NALOXONE DELIVERY |

This application relates to the following applications shown below in Table filed at USPTO on Dec. 31, 2024, which are incorporated herein by reference in its entirety.

| US application no. | Title of the Invention |
|---|---|
| 19/006,285 | ACTIVE IMPLANTABLE MEDICAL DEVICE (AIMD) SYSTEM FOR DRUG DELIVERY WITH FIXED DOSE SIZE |
| 19/006,301 | IMPLANTABLE DEVICE FOR ADJUSTABLE DOSE USING PRESSURE SENSOR FOR PISTON DISPLACEMENT MONITORING |
| 19/006,316 | IMPLANTABLE DEVICE HAVING PISTON DISPLACEMENT MONITORING |
| 19/006,338 | IMPLANTABLE DEVICE ACTUATED USING LEAD SCREW AND MOTOR |

TECHNICAL FIELD

This disclosure relates to devices, systems, and methods for precision drug dosing via an implantable drug delivery.

BACKGROUND

Poor medication adherence is a significant issue, leading to numerous hospital admissions and high healthcare costs. Factors contributing to nonadherence include poor insight, substance abuse, negative attitudes, side effects, and cognitive impairments. This problem is exacerbated among older adults on multiple medications, resulting in worsened health outcomes and increased mortality. Additionally, drug overdoses, particularly opioid-related, remain a severe public health crisis in the U.S., causing significant loss of life and economic burden.

Considering knowledge of a person skilled in art, there is a long-felt need to address the shortcomings in prior art and provide a system that is capable of implementing comprehensive strategies addressing issues related to clinical efficacy, toxicity, drug properties, and personalized drug dosing. It would be advantageous to have a system, method and device that considers at least some of the issues discussed above, as well as possibly other issues.

BRIEF SUMMARY

An embodiment relates to a system comprising an implantable device which is implanted inside a patient's body, configured to receive digital orders from a processor remotely located, one or more primary sensors and one or more secondary sensors configured to measure, retrieve and send patient's real-time data of bioactivity and drug concentration to the implantable device, and wherein the processor comprising a software-implemented module configured to operate remotely in cloud with an AI model to receive and analyze data from the implantable device, clinical records and patient's self-report to predict effects of drug usage, generate dosing recommendations, convert them into prescriptions for physicians to approve or reject, and control the implantable device to execute approved dosing plans.

An embodiment relates to a method comprising receiving pharmacokinetics data from a first database, receiving data on drug side effects, toxic concentration, disease side effects from a second database, training a machine learning model to identify a minimum effective concentration at which there is minimum side effect, generating a drug dosing model based on the trained model, and generating a software-implemented module to maintain a drug dosing via an implanted drug delivery device.

An embodiment relates to a method comprising identifying a drug that has stability, solubility and compatibility with an implantable device, loading the drug into the implantable device to form a drug-device combination, implanting the drug-device combination into a subject, releasing the drug in a controlled manner via the drug-device combination into body of the subject, monitoring an effect of the drug in the body of the subject, and accessing safety, tolerability, and pharmacokinetics of the drug in the body of the subject. The drug does not cause adverse reactions when in contact with the device and surrounding tissues and the implantable device safely delivers the drug over a prolonged period. In some embodiments, the method further comprises monitoring the drug-device combination for long-term safety and efficacy. In some embodiments, the method further comprises providing an alarm on occurrence of an adverse effect of at least one of the drug and the implantable device. In some embodiments, the method further comprises providing an alarm on occurrence of an error in release of the drug.

An embodiment relates to a clinical trial aid system comprising an implantable device which is implanted inside body of a subject, one or more sensors configured to measure, retrieve and send the subject's real-time data of bioactivity and drug concentration, a data storage device configured to store censored, analyzed and manually input data, an input module for receiving censored and input health data, a machine learning model for processing and analyzing received data, an output module for presenting instructions, data and other necessary information, a drug dosing module delivering drugs under directions from one of the machine learning module and authenticated input instruction, and a data storage module for storing and backing up all data for further study use, wherein the system is configured to monitor and retrieve real-time health data of a subject via one or more sensors, store the real-time health data in a first database, retrieve historical health data of the subject from a second database, deliver drug based on a personalized drug dosing regimen to body of the subject, and enable adjustment in the personalized drug dosing regimen by the machine learning model.

An embodiment relates to a system comprising an implantable device, a patch and a emergency caller wearable. The patch and implantable device are integrated with the emergency caller wearable (example: pendant type 911 caller). Someone going through overdose can activate the 911 calling pendant, which in turn activates the patch, which in turn activates the implantable device.

BRIEF DESCRIPTION OF THE FIGURES

These and other aspects of the present disclosure will now be described in more detail, with reference to the appended drawings showing exemplary embodiments of the present disclosure, in which:

FIG. 6 shows a flowchart of the process for drug precision dosing by the system, according to one or more embodiments.

FIG. 7A and FIG. 7B shows a flowchart of the process for drug precision dosing of Erythropoietin stimulating agent by the system.

FIG. 8 shows a system for clinical trial, according to one or more embodiments.

FIG. 9 shows a flowchart for a process of clinical trial via the implantable device, according to one or more embodiments.

FIG. 10 shows a process for drug repurposing via the system, according to one or more embodiments.

FIG. 11A illustrates an implantable device comprising a catheter, wherein the catheter is attached to the drug delivery outlet of the implantable device by sleeving the catheter over the drug delivery outlet.

FIG. 14 shows a schematic of a wearable emergency calling device, a smart patch and an implantable device, according to one or more embodiments.

FIG. 15 outlines steps for evaluating drug overdose using vital-signs evaluation with machine learning, according to one or more embodiments.

FIG. 16 outlines the process of evaluating drug overdose using vital-signs evaluation with machine learning, according to one or more embodiments.

DETAILED DESCRIPTION

Figure 1:
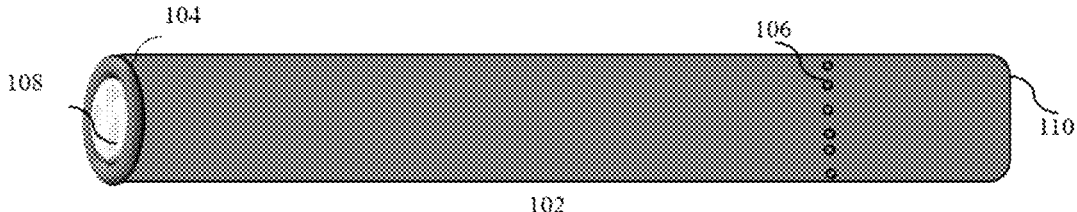
FIG. 1 shows an outside view of the implantable drug delivery device with a permeability module present at one end of said device.

An embodiment relates to a system functioning like an "autopilot" to deliver drug within body of a subject as prescribed and tailored to individual needs. The system comprises at least two of the four key components comprising a miniaturized implantable drug delivery device that dispenses drugs subcutaneously with controlled precision; a stable drug formulation that remains effective at body temperature; a biosensor that monitors drug levels and health markers, such as glucose, for real-time insights; and an analytics platform that analyses data to optimize drug delivery possibly in a real-time, ensuring highly personalized and effective patient care. The analytics platform integrates AI models and machine learning algorithms. In an embodiment, the system has at least three components as described above. In an embodiment, the system has all four components as described above.

The miniaturized implantable drug delivery device (referred to as device hereafter) is a medical device placed within the body for controlled delivery of drugs. It includes components such as a drug reservoir, control unit, and mechanisms for precise dosing and safety. In an embodiment, the implantable device of present disclosure is subcutaneously implanted within the body of the user, preferably in a human body. In the subcutaneous implant, the device is delivered under the skin into the subcutaneous tissue by surgery or injection and is used to deliver a drug for a long period of time. In some cases, the implantable device may be implanted transvenous. In some embodiments, the implantable device of the present disclosure is designed to deliver medication directly to a specific site or system in a controlled and sustained manner.

In an embodiment, the dose-to-dose variation of a drug via the device is ±25% or less by volume. In an embodiment, the dose-to-dose variation or flow discharge accuracy (used interchangeably throughout the specification) of a drug via the device is ±20% or less by volume. In an embodiment, the device has a dose accuracy of no wider than ±15% of the intended target dose.

In another embodiment, the flow discharge accuracy is ±10%. In another embodiment, the flow discharge accuracy is ±5%. In another embodiment, the flow discharge accuracy is ±3%.

"Drug" in context of the present disclosure may include any therapeutic active agent and/or a biologically active agent (i.e., an active ingredient in a pharmaceutical composition that is biologically active, such as a vaccine). Drug, that could be herein, is not limited by molecular weight of such agents. Terms "drug", "active agent", "therapeutic agent", "beneficial agent" or "pharmaceutical fluid" are used interchangeably. Drug as used herein refers to a single drug or multiple types of drugs. The drug formulation allows controlled delivery of the drug from an implanted delivery device over sustained periods of time, even when such delivery occurs at low flow rates, through microhole/s. The formulation comprises a therapeutic drug and a drug carrier. The therapeutic drug is one of an analgesic agent, an anti-inflammatory agent, a steroid drug, an anti-viral drug, a cytotoxic agent, an anti-diabetic drug, an anti-depressant, a non-stimulant drug, an anti-arthritis and anti-rheumatic drug, a blood pressure control related drug, an autoimmune disease-related drug, or weight loss/obesity related drugs. In an example, the drug is naloxone. In another example, the drug is ketamine. In another example, the drug is semaglutide. In another example, the drug is exenatide. In another example, the drug is ketamine. In another example, the drug is oxycodone. In another example, the drug is naltrexone. In another example, the drug is an antipsychotic drug.

In an embodiment, the drug formulation remains stable for at least 3 months to 5 years at body temperature.

The biosensor comprises one or more sensors that monitor various physiological parameters, physical parameters, and biomarkers to provide feedback on the body's condition and response to treatment. The term "Biomarker" (e.g., glucose levels, heart rate, drug concentration) refers to a measurable indicator of a biological state or health condition, often used to track the effectiveness or side effects of a drug. The term "health condition" refers to a specific medical condition or disease for which the drug is being used as a treatment.

For greater reliability, a multi-sensor fusion system integrates data from various sources, leveraging deep sensor fusion neural networks. The term "multi-sensor fusion system" refers to a configuration of multiple sensors working together to provide data that is more precise, reliable, and comprehensive compared to using a single sensor alone. This improvement is achieved by combining readings from different sources, thereby reducing uncertainties, compensating for individual sensor limitations, and enhancing the overall quality of information. Auxiliary non-invasive external sensors, such as wearable glucose monitors, are used for auxiliary monitoring and to synchronize data using normalization algorithms and supplement implanted device readings. Auxiliary monitoring refers to the use of additional external, non-invasive sensors to complement the primary monitoring system. These sensors provide supplementary data on physiological parameters, environmental conditions, or other relevant factors that may influence drug dosing and treatment response. Auxiliary monitoring supports enhanced decision-making by offering a broader and more holistic view of the patient's status.

In some embodiments, the system integrates artificial intelligence with real-time patient data to develop an intelligent management assistant tailored for a specific health condition. By employing predictive algorithms and advanced modeling approaches, the system forecasts critical biomarkers associated with the condition, enabling proactive treatment planning. This intelligent assistant provides personalized treatment strategies based on predicted trends while dynamically adapting to changes in patient data, ensuring optimized and responsive care tailored to individual needs.

In an embodiment, the implantable drug delivery device has different modules such as, without limitation, a sensor module, a drug module, a valve module, an electronics module, and a power module. The device may further comprise a permeability module. The permeability module may comprise a semi-permeable membrane. The device may comprise an osmotic agent chamber that may contain or be configured to contain an osmotic solution. These modules are interconnected with each other. A person skilled in the art would understand different ways of interconnecting these modules, such as but not limited to screwing them together, creating notches at the ends of the modules, etc. In some embodiments, each module is threaded with male-female threads such that the first module screws into the second module, the second module screws into the third module, and the third module screws into the fourth module.

In an embodiment, upon operation of the power supply module of the device: (i) the permeability module allows inflow of fluid from the semi-permeable membrane into the osmotic agent chamber to establish an osmotic pressure, (ii) the electronic module is configured to switch on and off the valve module as per a predetermined program set within the device to regulate flow of the drug from the drug chamber. In an embodiment, the inflow of a fluid through the semi-permeable membrane into the osmotic agent chamber is on a real-time basis. In an embodiment, the implantable device has a compressible piston. In an embodiment, the device has no compressible piston. In an embodiment, the device does not have a permeability module.

FIG. 1 shows an outside view of the implantable device. The device has a tubular structure. It has a first end 108, and a second end 110. As shown in FIG. 1, the device comprises an outer casing 102, a permeability module 104 at the first end, and one or more drug outlets/orifices 106 for release of the drug. The casing 102 is generally a tubular element. The casing surrounds the device except the first end 108 having the permeability module 104. Dimensions of the device are such that the sub-cutaneous implantation of the device in a mammal or more specifically a human could be achieved. In an embodiment, the breadth of the casing is between 3 mm to 5 mm, such as 3 mm, 3.5 mm, 4 mm, 4.5 mm etc. In an embodiment, the length of the casing is between 2.5 cm to 10 cm, such as 4 cm, 5 cm, 6 cm, 7 cm, 8 cm, 9 cm or 10 cm or preferably 4 cm to 8 cm. The permeability module 104, along with other functions, primarily seals the interior of the implantable device from the first end 108, allowing only specific liquid molecules to permeate through a membrane plug into the device's interior. In an embodiment, the permeability module 104 also effectively prevents items within the implantable device, such as an osmotic agent, to backflow outside the device. The permeability module 104 at the first end allows ingress of the fluid into the device and is coupled to the osmotic agent chamber. The permeability module is designed to separate solutes from a feed solution, such as blood serum, using a semi-permeable membrane. In an embodiment, the osmotic agent chamber is adapted to include an initial chemical composition (e.g., one or more ion species) that functions to alter osmotic pressure within the osmotic compartment(s) upon fluid (such as water from the body fluid) migration across the permeability module.

Figure 2:
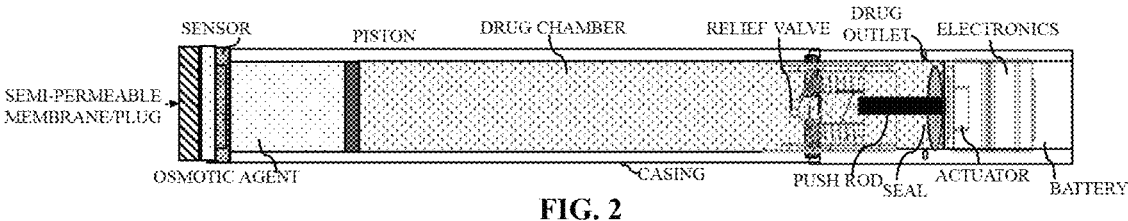
FIG. 2 shows an inside view of the implantable drug delivery device in a valve open state, according to one or more embodiments of the disclosed disclosure.

Referring to FIG. 2, it shows an inside view of the implantable drug delivery device according to one or more embodiments of the disclosure. The device, comprises a permeability module comprising a semi-permeable membrane at one of the device, an osmotic agent chamber comprising an osmotic solution, a sensor module comprising a sensor configured to monitor a physical parameter, a drug chamber comprising a drug, a piston sandwiched between the osmotic agent chamber and the drug chamber, a valve module (relief valve, push rod, seal, actuator) to allow unidirectional flow of the drug from the drug chamber to outside the device through one or more drug outlet orifices present within the device, an electronic module, and a power supply module, wherein upon operation of the power supply module of the device the permeability module allows inflow of a fluid from the semi-permeable membrane into the osmotic agent chamber to establish an osmotic pressure, the electronic module configured to switch on and off the valve module as per a predetermined program set within the device to regulate flow of the drug from the drug chamber. The implantable device has a tubular structure having an outermost casing. In an embodiment, the casing is made up of a biocompatible material or FDA approved material, such as, without limitation, titanium. In an embodiment, the casing has housing to connect different modules. As per a principle of operation of the implantable, a person skilled in the art would understand different ways of putting electrical circuits in the casing, such as, but not limited to, gluing or imprinting. In some embodiments, the housing material provides durability, corrosion resistance, and compatibility with body and fluids within the device, such as, but not limited to, titanium.

In an embodiment, the device tube has an outer diameter between 3 mm to 5 mm, such as 3 mm, 3.5 mm, 4 mm, 4.5 mm etc. In an embodiment, the casing has a wall thickness about 0.25 mm, 0.3 mm, 0.4 mm, 0.5 mm, 0.6 mm, 0.7 mm, 0.8 mm, 1 mm.

In some embodiments the implantable device comprises one or more sensors built-in the device to monitor at least one of a device parameter, one or more drug relevant metabolites, and drug levels in subject's body. As used herein, "Primary sensors" are the sensors attached to the implantable device. As used herein, "Secondary sensors" are the sensors not attached to the implantable device but used for system predictions and recommendations.

Figure 3:
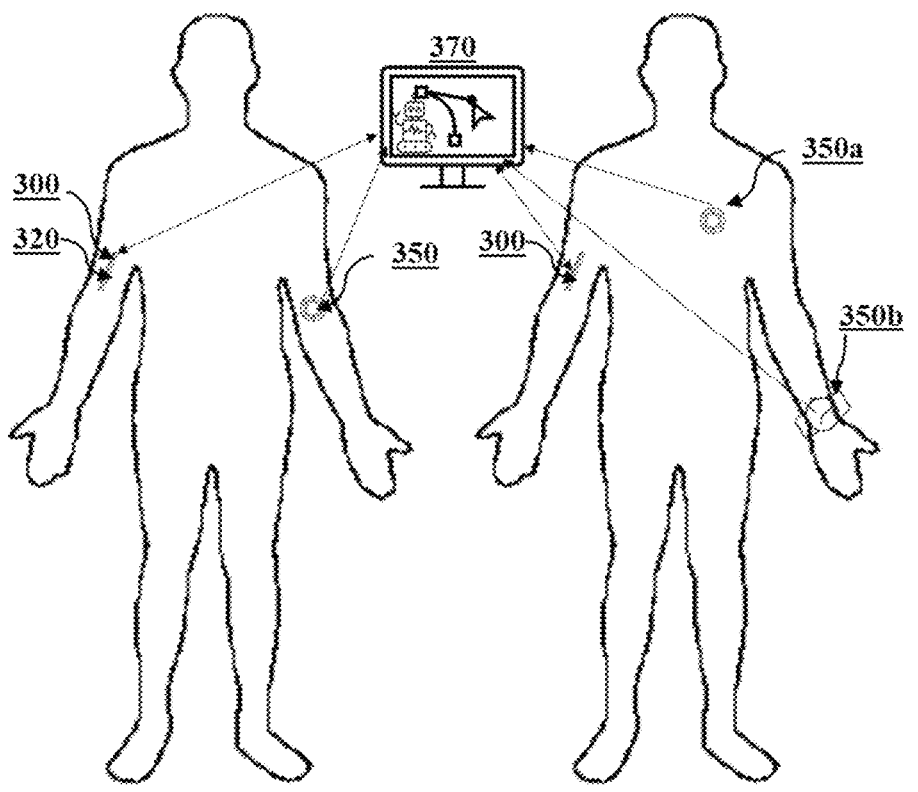
FIG. 3 shows a system comprising an implantable device, primary sensors and/or secondary sensors, and a processor, according to one or more embodiments.

Referring to FIG. 3 shows a system comprising an implantable device, primary sensors and/or secondary sensors, and a processor, according to one or more embodiments. The system comprises an implantable drug delivery device 300 comprising one or more primary sensors 320, one or more secondary sensors 350, 350*a*, 350*b*, and a software-implemented module 370. The software-implemented module 370 operates remotely in the cloud. The software-implemented module 370 comprises an analytics platform that is configured to analyze data from the implantable device 300, one or more primary sensors 320, and one or more secondary sensors 350, 350*a*, 350*b*, (optionally a clinical relevant database, and the subject's electronic medical record (EMR)) to process data using prediction and recommendation algorithms for precision dosing. The term "Analytics platform" refers to a computational system that processes data from the implanted device and sensors to optimize drug regimens, predict adverse effects, and analyze treatment outcomes using techniques like AI and machine learning.

In an embodiment, the device for controlled drug delivery can maintain drug concentrations below the toxicity threshold by employing precise dosing mechanisms that ensure the release of steady, calibrated amounts of the drug within the therapeutic window. The term "toxicity threshold" refers to the specific concentration of a drug in the body above which it becomes harmful and may lead to adverse effects or toxicity.

The device can be equipped with programmable micropumps or valves that dispense the drug at predefined intervals and amounts, ensuring a consistent concentration in the bloodstream. Real-time biosensors can monitor drug levels or physiological biomarkers, enabling the device to adjust the release rate dynamically to avoid exceeding the toxicity threshold.

In an embodiment, the device is equipped with a programmable chip and/or wireless communication chip. The chip is configured to communicate with outside world.

In some embodiments, using biocompatible and degradable materials in drug reservoirs can facilitate controlled diffusion, allowing gradual release over time.

In some embodiments, the implantable device is integrated with AI-Driven control systems that analyze patient-specific data and optimize dosing schedules based on individual metabolic rates, ensuring that the drug stays within the therapeutic range. The system can be remotely controlled for adjustments and includes safety features like automatic shutoff to prevent overdose. This approach ensures effective treatment while minimizing the risk of adverse effects, particularly in drugs with narrow therapeutic windows.

FIG. 4A, FIG. 4B, FIG. 4C and FIG. 4D, show various dosing schemes that could be used to maintain substantially constant drug concentration profile in a human body below the concentration of drug above which the risk of side effects increase, according to one embodiment disclosed herein. The term "dosing schemes" refers to the specific patterns or regimens by which a drug is administered over time, including factors like frequency, dose, and duration, to achieve a desired therapeutic effect while minimizing risks. The term "constant drug concentration profile" refers to a stable or consistent level of the drug in the bloodstream over time, ideally within a therapeutic range that ensures effectiveness without causing toxicity or side effects.

Figure 4A:
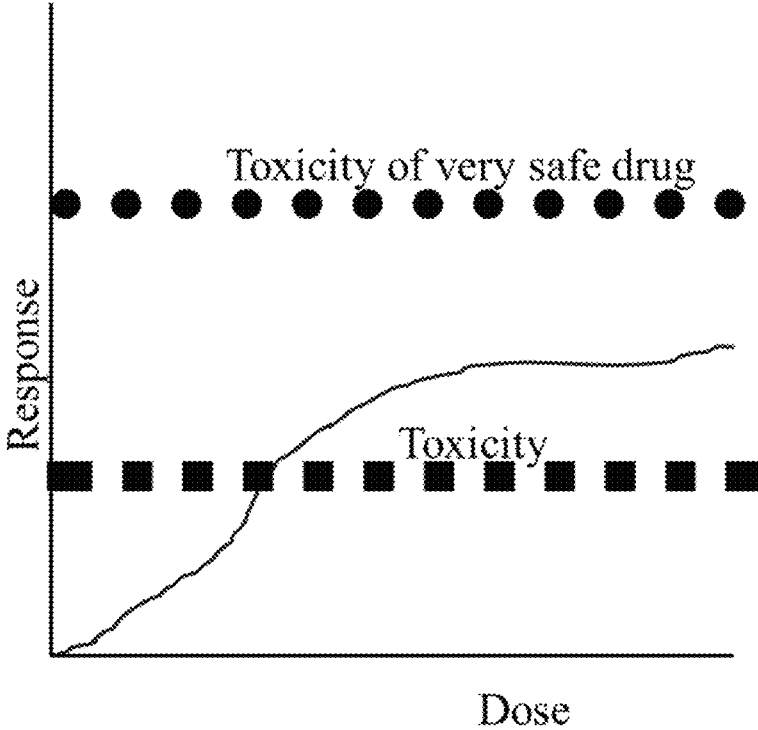
FIG. 4A illustrates drug dosing at a minimal toxicity level, lower than that of a very safe drug for a similar condition.

As shown in FIG. 4A, the drug dosing through the implantable device is maintained at a minimal toxicity level, which is lower than the toxicity threshold of a well-established, very safe drug used for a similar health condition. The term "minimal toxicity level" refers to a drug concentration that is kept sufficiently low to avoid reaching the toxicity threshold, thus reducing the likelihood of side effects while still providing therapeutic benefits. The term "very safe drug" refers to a medication that has been well-established in clinical use with a wide therapeutic window, meaning it can be used safely without significant risk of harmful side effects under normal conditions.

Figure 4B:
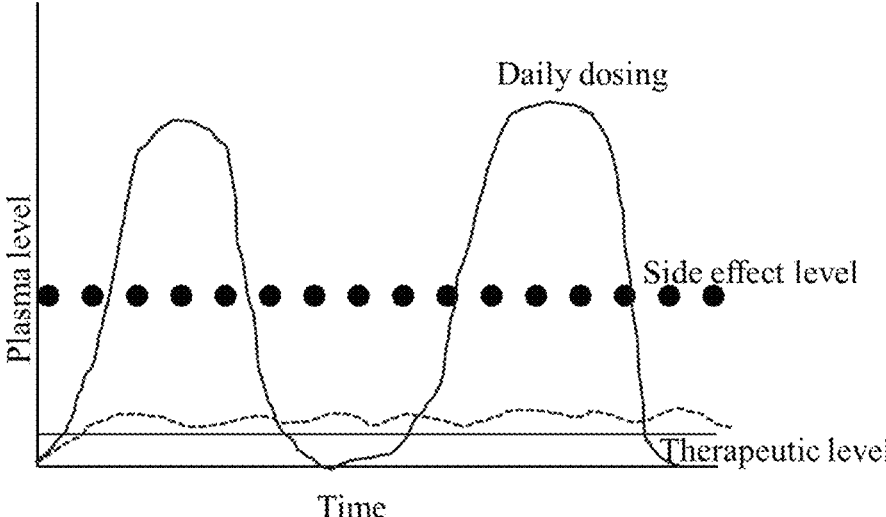
FIG. 4B shows daily dosing optimized for therapeutic efficacy with controlled side effects.

In an embodiment, in FIG. 4B, daily dosing of the implantable device is optimized to achieve therapeutic efficacy by administering the drug at the appropriate therapeutic level while keeping side effects consistently low. For drugs like insulin, implantable devices will monitor blood glucose levels and adjust insulin delivery accordingly. For opioids or cancer treatment drugs (e.g., Morphine or chemotherapy agents), the device could adjust delivery to maintain a steady, low concentration in the bloodstream to reduce side effects like addiction or toxicity, ensuring therapeutic efficacy without reaching harmful levels.

Figure 4C:
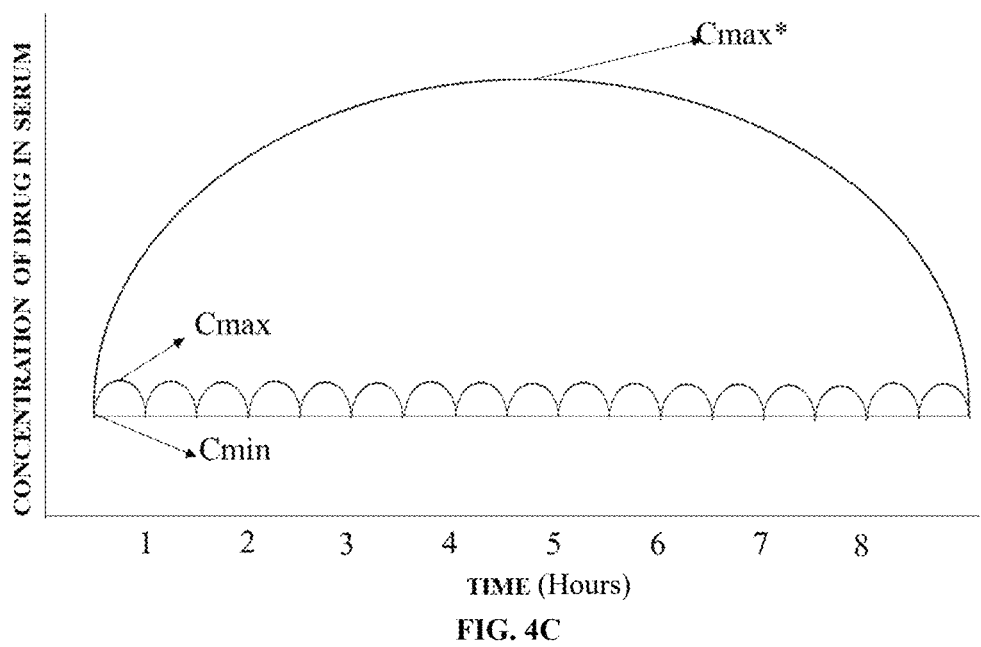
FIG. 4C shows a schematic that maintains a substantially constant drug concentration profile below the concentration of drug above which the risk of side effects increase, according to one embodiment disclosed herein.

As shown in FIG. 4C, $C_{min}$ is the minimum concentration of the drug, below which the drug may not be effective at controlling the target condition. $C_{max*}$ is the concentration of drug above which the risk of side effects increases. $C_{max}$ is a concentration between $C_{min}$ and $C_{max*}$ that provides an effective and tolerable therapy. The device is configured to maintain the concentration at $C_{max}$ in an embodiment. If the concentration is above $C_{max}$, the drug flow is stopped; if the concentration goes below a $C_{min}$, the drug flow is allowed. The concentration of the drug is maintained between a concentration range of $C_{min}$ and $C_{max}$ with drug flow modulated based on real-time monitoring in the body of the subject. The term "real-time monitoring" refers to the continuous observation and analysis of physiological parameters and drug levels, enabling immediate identification of deviations from the recommended therapeutic range. This facilitates timely adjustments, such as modifying the drug delivery rate or dosage, to maintain the drug's therapeutic effectiveness and prevent underdosing or overdosing, ensuring optimal patient outcomes.

In some embodiments, a first sensor is used to monitor a first concentration of a drug delivered by the device and a second sensor is used to monitor a second concentration of one or more bioactivity markers. The one or more bioactivity markers comprise at least one of a drug side effect marker and a target disease marker. The drug is used to cure the target disease. The $C_{max}$ is adjusted such that at least one of a disease marker and a drug effect marker is at a concentration below a predefined threshold concentration or is equal to zero and the drug concentration is below $C_{max*}$.

Figure 4D:
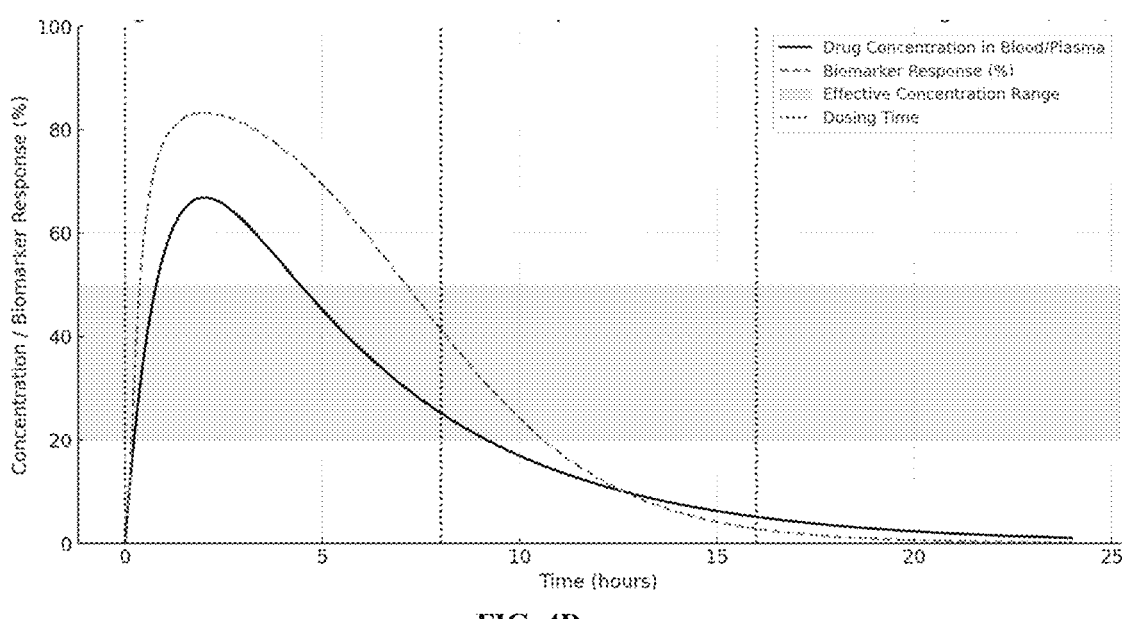
FIG. 4D shows drug dosing profile in blood/plasma.

FIG. 4D illustrates a relationship between drug concentration in blood/plasma and a biomarker associated with adverse effects, according to one or more embodiments. The solid black curve in the graph represents the drug concentration over time, starting high after administration and gradually decreasing due to elimination from the body, and the dashed gray curve shows the biomarker response, which increases with drug concentration and indicates potential adverse effects at higher levels. The shaded gray region denotes the effective drug concentration range, where the medication achieves therapeutic benefits while minimizing adverse effects, and the vertical dotted lines indicate dosing time to maintain the drug concentration within the effective range. The dosing profile ensures the drug concentration stays within the therapeutic window to optimize efficacy and minimize adverse effects. This graph highlights the importance of appropriate dosing intervals to ensure the drug remains effective without exceeding levels that could trigger significant adverse effects.

An embodiment relates to a system for personalized drug dosing. The term "personalized drug dosing" refers to dosing according to an individual needs.

The system has an analytics platform having an input module, configured for collecting and storing data from one or more of a clinical record, an implanted sensor, and a drug effect information database. The analytics platform process collected data and generate drug dosing recommendations. In some embodiments, the analytics platform comprises AI model that is trained to process system-collected data, configured for establishing prediction algorithms, and generate drug dosing recommendations and achieve self-refinement by reinforcement learning with feedback loop, an output module, configured for sending recommendations to patients and medical professional individuals for approval, as well as updates of any error and warning raised by the system; and a drug dosing module, configured for operating a dosing of drugs, and for controlling type, amount, timing and frequency of the dosing to the patients when prescription is approved by the physicians. The term "feedback loop" refers to a system design where output data is analyzed and fed back into the system to refine processes, such as improving AI models or adjusting dosing protocols.

Data is transmitted securely using robust communication protocols such as Bluetooth, Wi-Fi, or cellular networks, optimized by adaptive communication selection algorithms. Fail-safe systems automatically halt operations during anomalies using rule-based safety triggers. The term "fail-safe system" refers to a safety feature designed to stop or alter drug delivery in the event of system anomalies (Anomalies comprises at least one of a device failure, bidirectional data acquisition failure or a glitch in analytics platform) or detected risks, ensuring patient safety. These devices feature broad-spectrum sensors that monitor multiple physiological parameters like glucose levels and heart rate, employing sensor fusion algorithms such as Kalman Filters for enhanced accuracy.

A continuously updated drug effect information database enables predictive insights into patient responses, supported by federated learning models for secure updates. "Drug Effect Information Database" refers to a repository that stores information on drug behavior, interactions, efficacy, and side effects. It can be updated with real-world patient data, including demographic information, medical history, comorbidities, genetic profiles, treatment responses, and adverse event reports. Incorporating such data improves the database's accuracy and relevance, enhancing drug safety, personalization of treatment, and overall effectiveness in diverse patient populations. Advanced analytics platforms optimize dosing regimens and predict adverse effects using machine learning models like Random Forest, XGBoost, and LSTM networks for analyzing temporal data. The machine learning models are trained to analyze data, identify patterns, and predict outcomes like drug interactions, adverse effects, and optimal dosing regimens. Integration of historical and real-time data enhances predictive accuracy with Bayesian Networks, while long-term-effectiveness tracking leverages time-series models like ARIMA and Prophet. Automatic dosing adjustment adapts medication delivery based on patient responses through reinforcement learning algorithms such as Q-Learning.

The system may include an input module for collecting user-provided data, enhanced with natural language processing (NLP) to interpret inputs effectively. Population-level insights are derived using clustering algorithms like K-Means, while pharmacokinetic/pharmacodynamic (PK/PD) modeling predicts drug behavior using PBPK (Physiologically Based Pharmacokinetic) modeling. Adaptive algorithms, including Gradient Boosting, refine treatments over time, ensuring optimal outcomes. The term "adaptive algorithm" refers to a dynamic computational method that learns and adjusts dosing recommendations over time based on individual patient data and responses. Data security is paramount, with HIPAA-compliant storage implemented via end-to-end encryption methods like AES-256. The term "HIPAA-compliant data storage" refers to a secure method of storing patient data that adheres to the health insurance portability and accountability act (HIPAA) standards for privacy and security.

Mobile apps and wearable device interfaces allow users to monitor their treatments conveniently, employing UX personalization algorithms and gamification to encourage adherence. The term "wearable device interface" refers a user-friendly interface on devices like smartwatches or fitness trackers that allow patients or healthcare providers to access the data for different applications such as viewing treatment metrics, receiving alerts, and/or inputting data in the said device. For providers, dashboard systems deliver real-time insights and alerts, supported by event-driven architecture. Integration with electronic health records (EHRs) ensures seamless workflows using FHIR (Fast Healthcare Interoperability Resources). Compatibility with consumer wearables adds value, combining activity and sleep data through multi-modal data analysis.

To ensure therapeutic efficacy, continuous drug concentration monitoring employs chemometric analysis for real-time tracking, while energy-efficient designs incorporate wireless charging and AI-driven dynamic power management. Dynamic adaptation to patient responses is achieved using control theory, ensuring personalized care. Healthcare provider applications assist clinicians with treatment recommendations, supported by predictive analytics models.

In some embodiments the system uses AI-based prediction models for drug interaction and personalized risk assessment. Personalized risk assessment refers to the evaluation of an individual's unique susceptibility to adverse effects, drug interactions, or suboptimal treatment outcomes based on their specific physiological, genetic, and biomarker data. It involves analyzing patient-specific factors, such as co-existing medical conditions, current medications, lifestyle, and historical responses to treatments, to predict potential risks and guide safe and effective therapy. In the context of developing personalized treatment regimens, personalized risk assessment enables the identification of the safest and most effective drug dosing strategies tailored to the individual. This ensures that the treatment minimizes risks while maximizing therapeutic benefits. These models use machine learning algorithms to analyze large datasets, including pharmacological properties, patient history, and real-time physiological data, to predict potential drug-drug or drug-food interactions, assess the likelihood of adverse events or inefficacy, and support dynamic optimization of treatment regimens for individualized care.

The system also includes an expanded drug interaction database utilizing knowledge graphs to map relationships, and a patient-preferences module that customizes treatments using multi-criteria decision-making (MCDM) algorithms. Data security during communication is reinforced with public key infrastructure (PKI), ensuring confidentiality. Real-time data integration combines historical and live data using hybrid AI models, enabling predictive analytics and optimized dosing.

For adverse event management, anomaly detection algorithms like Autoencoders identify potential risks, generating alerts and feedback through machine learning-based thresholds. Training models are designed to identify the minimum effective drug concentration using multi-objective optimization, balancing efficacy with safety. Lastly, the system supports advanced clinical trial systems, combining reinforcement learning and Generative Adversarial Networks (GANs) to simulate trial outcomes and optimize drug development.

This comprehensive ecosystem integrates cutting-edge AI and machine learning techniques with robust hardware design to deliver personalized, precise, and secure drug delivery solutions tailored to patient needs.

In some embodiments, Algorithms such as PID (Proportional-Integral-Derivative) control and anomaly detection (e.g., Isolation Forest) ensure precise and safe operation of the device. A drug reservoir management subsystem detects low drug levels, alerting users or providers through threshold-based algorithms and redundancy checks. To maintain functionality, a self-cleaning mechanism employs ultrasonic waves or hydrophobic coatings to prevent blockages, supported by predictive maintenance algorithms. In some embodiments, the AI model could be operated remotely in the cloud.

Figures 5A, 5B:
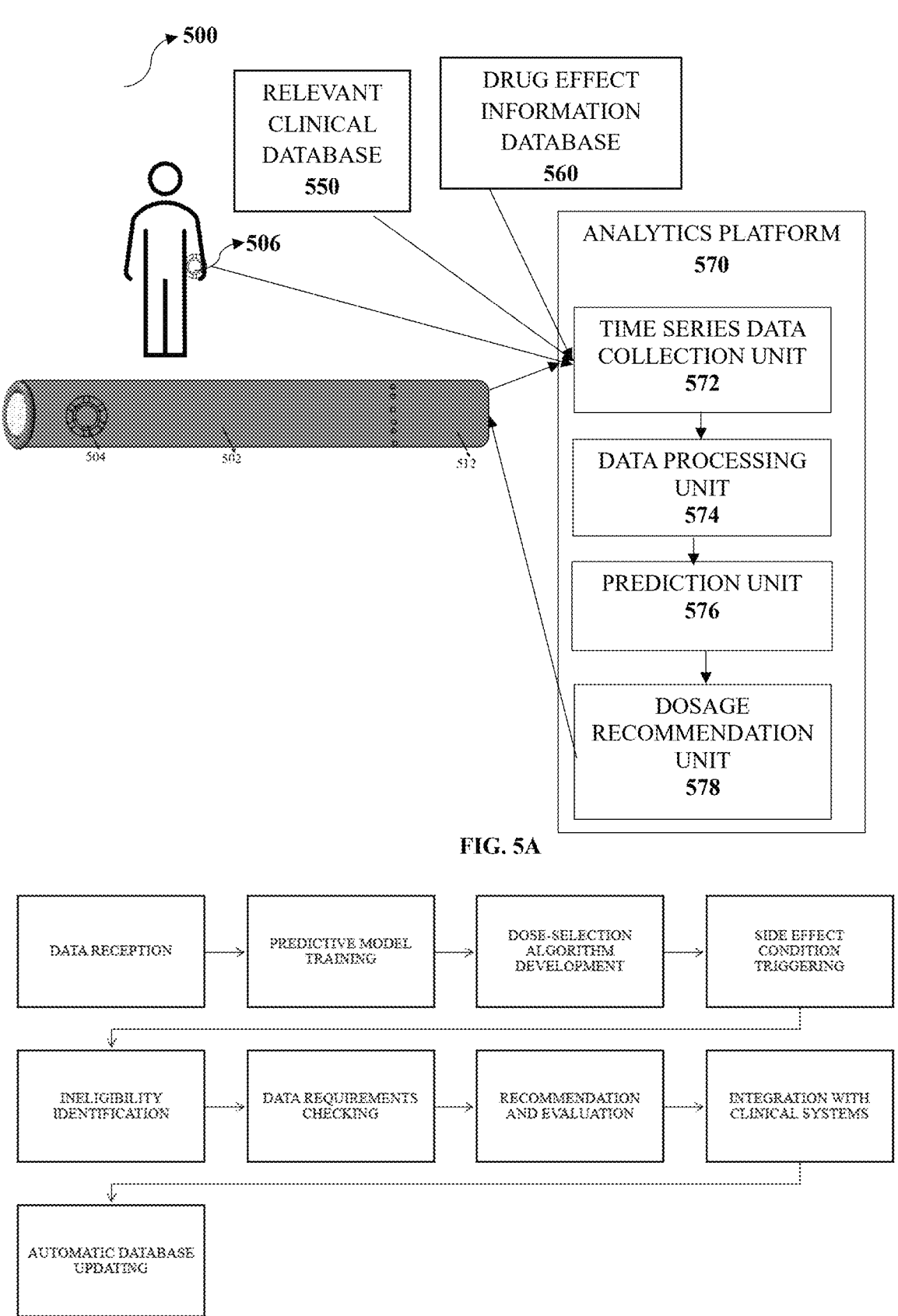
FIG. 5A shows a system for drug precision dosing of a drug, according to one or more embodiments.
FIG. 5B shows model informed precision dosing framework.

Referring to FIG. 5A, it shows a system 500 for precision dosing of a drug, according to one or more embodiments. The system comprises an implanted drug delivery device 502 comprising an electronic module, one or more biosensors 506, a drug effect information database 560, and an analytics platform 570 comprising an input module. In some embodiments, the implanted drug delivery device comprises built-in biosensors 504 that monitor physiological parameters and biomarkers, electronics module 512 further comprising a communication unit for real-time data acquisition and a control unit to manage drug delivery. Data from the device and the one or more biosensors continuously stream to an analytics platform via an input module, which provides live updates, alerts, and control options. The analytics platform may further comprise a time series data collection unit 572, a data processing unit 574, a prediction unit 576 and a dosage recommendation unit 578. Time series data collection unit 572 is configured for continuous acquisition and storage of real-time data over a period. It organizes physiological parameters, biomarker readings, and device performance metrics into structured time series datasets. These datasets provide a chronological view of patient-specific trends and patterns, which are essential for monitoring changes and understanding the temporal relationship between drug delivery and physiological responses. The data processing unit 574 is configured to process the raw data collected by the time series data collection unit. It performs filtering, normalization, and aggregation to eliminate noise, ensure consistency, and prepares the data for analysis. The processed data is further categorized based on biomarkers and parameters, enabling the extraction of relevant features critical for downstream analytics. Using advanced algorithms, including machine learning and statistical models, the prediction unit 576 analyzes historical and real-time data to forecast future trends in patient responses. For example, it predicts potential changes in biomarker levels, physiological states, or the onset of adverse reactions. These predictions are instrumental in anticipating the effects of drug delivery and making proactive adjustments to the system. Based on insights from the prediction unit and predefined therapeutic thresholds stored in the drug effect information database 560, the dosage recommendation unit generates precise dosage recommendations. It factors in the patient's current condition, predicted physiological changes, and drug pharmacokinetics to propose adjustments to drug delivery in real time. The recommendations are transmitted to the control unit within the drug delivery device for implementation, ensuring optimal therapeutic outcomes while minimizing risks. The system logs all data securely through a data logging mechanism to maintain accuracy and compliance. The analytics platform processes this data, utilizing statistical models and/or AI models to optimize dosing regimens, predict adverse events, and analyze treatment responses. Algorithms like Logistic Regression, Random Forest, and Gradient Tree Boosting refine trial parameters and enhance decision-making. The system adapts dynamically to individual patient responses, enabling personalized treatment while identifying population-level trends and actionable insights. By integrating advanced drug delivery, real-time monitoring, and sophisticated analytics, the system supports adaptive clinical trials, accelerates drug development, and improves patient safety.

Referring to FIG. 5B, the process for personalized drug dosing via an implantable drug delivery device begins with data reception from in-built biosensors present in the implantable device that captures real-time physiological parameters and drug levels. A predictive model trains on this data to forecast patient-specific responses and optimize dosing. A dose selection algorithm continuously refines dosage based on predictive insights, ensuring therapeutic efficacy while minimizing risks. Side effect conditions trigger alerts when adverse thresholds are detected, prompting immediate intervention. Ineligibility identification filters out unsuitable dosing regimens for patients based on their real-time responses and historical data. The system checks for additional data requirements, ensuring comprehensive inputs for accurate predictions. Recommendations are generated and evaluated against predefined clinical outcomes for validation. Integration with clinical systems allows seamless communication and operational adjustments, while an automatic database updating mechanism ensures all dosing and response-data remain accurate and up-to-date for ongoing and future use.

Referring to FIG. 6, it shows a flowchart of the process 600 for drug precision dosing by the system. The software-implemented module within the system executes a series of method steps. Step 602 comprises receiving data from the implantable device, the one or more secondary sensors, and external databases. The system actively gathers clinical records 602.1, ensuring a continuous influx of relevant data 602.2, 602.3. The system implements secure and ethical data access protocols, ensuring patient consent and de-identification are maintained. Step 604 comprises preprocessing the received data. Preprocessing data 604 comprises handling missing data 604.1, normalizing or scaling features 604.2 and encoding categorical variables 604.3. The system handles missing data in real-time 604.1, ensuring the integrity of the dataset. Established data quality control methods can be used to conduct completeness and consistency checks. Missing data imputation techniques, based on either domain knowledge or statistical methods, can be employed. Feature engineering techniques may be utilized for dimensionality reduction and improved model interpretability. It may ensure ongoing data quality and completeness, maintaining a high standard for the collected information. The module may further select and update relevant features (parameters) crucial for model training and prediction. Step 606 comprises selecting an appropriate data processing algorithm. The module chooses the most appropriate machine learning algorithm 606.1 based on the latest data characteristics. It can dynamically split the incoming data into training and testing sets 606.2 to maintain model accuracy. The system initializes the model 606.3 with up-to-date hyperparameters, optimizing performance based on the current data distribution. Random forests, logistic regression, support vector machines, and deep learning models like neural networks can be used based on specific tasks and data characteristics. Step 608 comprises training the model. The system actively trains the model on the latest training set 608.1, incorporating new information for improved accuracy. Validation occurs on a separate, dynamically updated validation set 608.2 to ensure the model's ongoing reliability. The module adjusts hyperparameters 608.3 in real-time, optimizing the model for the current dataset. Gradient descent with various optimizers like Adam or RMSprop can be used for model training. Step 610 comprises evaluating the model. Ongoing evaluation of model performance is conducted on the testing set 610.1, adapting to the evolving data landscape. Metrics, such as mean absolute error, are continuously assessed 610.2 to gauge the model's effectiveness. Step 612 comprises developing and refining the dose-selection algorithm. Rule-based systems, decision trees, or reinforcement learning algorithms are used for dose-selection based on clinical guidelines and model predictions 612.1. The system develops a separate, well-defined dose-selection algorithm based on clinical guidelines 612.2, pharmacodynamics, and model predictions. Rigorous testing and validation of the dose-selection algorithm are performed before deployment. Step 614 comprises model deployment. The model is deployed in a suitable environment 614.1, adapting to changes in clinical workflows and requirements. Deployment of the model and algorithm occurs in a controlled environment with human oversight and safety protocols. An approval process for algorithm updates is implemented to ensure thorough testing and risk mitigation. Continuous integration with clinical systems 614.2 ensures seamless interoperability. Real-time or periodic updates 614.3 are implemented to keep the deployed model current and effective. Step 616 comprises recommending a drug dose. Transparent and interpretable model outputs on user friendly user interfaces enable physician-informed decision-making 616.1. User interfaces facilitate easy incorporation of physician feedback and implement adjustments 616.2 as well. Step 618 comprises administering a drug dose to a subject. The system administers prescribed drug doses to patients 618.1 based on real-time recommendations. Continuous monitoring of patient responses and adverse effects 618.2 enables ongoing adjustments to the dosing strategy. Step 620 comprises feedback looping. The system continuously gathers new clinical data 620.1, facilitating a dynamic feedback loop. Periodic model retraining 620.2 is performed based on the latest data, ensuring the model remains relevant and accurate over time. Data feedback loops capturing both recommended and actual doses, as well as patient outcomes, are utilized. The feedback loop data is used for continuous model retraining and performance improvement.

In an embodiment, the system integrates artificial intelligence and real-time patient data to develop an intelligent Anemia Management Assistant (AMA). The system employs predictive algorithms with highly sophisticated modeling approaches to forecast Hemoglobin (Hb) levels in End-Stage Kidney Disease (ESKD) patients. The AMA not only offers personalized treatment plans aligned with predicted Hb trends but also adapts dynamically by adjusting treatment strategies based on ongoing patient data.

In an embodiment, a system comprising an implantable device for controlled release of erythropoietin stimulating agent, a noninvasive total hemoglobin monitoring sensor, and an artificial intelligence decision support module is provided. The artificial intelligence support module comprises an anemia control model (ACM) that is configured to recommend a dose of erythropoietin stimulating agent based on a patient's profile. The patient profile comprises one or more of sex, height, previous delta hemoglobin, ferritin, transferrin saturation index, albumin, phosphate, leukocyte, C-reactive protein, mean corpuscular volume, mean corpuscular hemoglobin, calcium, sodium, potassium, dry body weight, predialysis weight, online clearance monitoring $K_T/V$, Darbepoetin doses, and iron doses. The system employs multidimensional data analysis techniques, integrating data collection, aggregation, and analysis to characterize drug-response variability at the individual level. This comprehensive approach involves the use of precise drug delivery devices and is orchestrated by clinical pharmacology experts. The system's ability to analyze multidimensional data enables it to contribute significantly to personalized healthcare by facilitating precision dosing, allowing for the tailoring of drug doses to individual patient needs.

Referring to FIG. 7A and FIG. 7B, it shows a flowchart of the process for drug precision dosing of Erythropoietin stimulating agent (ESA) by the system. Step 702 of the method 700 comprises receiving data from clinical records through a relevant clinical database (e.g., EuCliD) and receiving patient's profile from a health record database. Step 704 of the method 700 comprises training the predictive model by utilizing machine learning on a specified number (N) of clinical records, validating the model on a set number (X) of records, and evaluating the model's mean absolute prediction error (e.g., 0.59 g/dl for ESA). Step 706 of the method 700 comprises developing a dose-selection algorithm. The algorithm considers the parameters and rules adhering to clinical guidelines for anemia treatment in hemodialysis patients, simulating drug doses on the predictive model, selecting doses that move hemoglobin (Hb) to the target interval, and avoiding excessive Hb decreases or increases. Step 708 of the method 700 comprises triggering ACM condition. This step further comprises triggering on a new HB value and checking patient eligibility criteria for dosage variations. The non limiting examples of eligibility criteria are a) age greater than 18, b) no admission in the last 90 days, c) no transfusion in the last 90 days, and d) a minimum of 27 out of the expected 39 dialysis treatments received. Step 710 of the method 700 comprises identifying ACM ineligibility condition, such as age less than 18, admission in the last 90 days, receiving a transfusion in the last 90 days, and not receiving a minimum of 27 dialysis treatments out of the expected 39 treatments. Step 712 of the method 700 comprises checking data requirements. This step comprises checking clinical data for the past 90 days and obtaining complete information on various drugs administered during the specified period. Step 714 of the method 700 comprises receiving information on patients deemed ineligible for ESA therapy from a user interface (e.g. physician's user interface). Step 716 of the method 700 comprises recommending a drug dose based on the latest model predictions. Subsequently, physicians evaluate the validity of these recommendations on an individual basis and decide whether to accept the provided therapy recommendations or formulate a different drug dose/prescription. Step 718 of the method 700 comprises the integration of NephroCare clinics, including a dedicated module in the clinical database specifically designed for drug suggestions. Accepted suggestions seamlessly transition into actual prescriptions, while rejected suggestions require a reason from the physician. Step 720 of the method 700 comprises updating database automatically. The establishment of an automatic interface module with the clinical database facilitates the continuous feed of updated clinical data to the ACM. This ensures that the predictive model remains informed by the latest clinical information, contributing to the accuracy and relevance of therapy recommendations.

In an example, a system comprising an implantable device for controlled release of Semaglutide, a non-invasive hydration sensor, and an artificial intelligence decision support module. The semaglutide concentration in the blood is measured via one or more sensors or estimated by the system using measurement of the osmotic unit movement. The system actively personalizes semaglutide dosing through the implantable drug delivery device. The implantable device continually collects real-time physiological data, including blood glucose, heart rate, and weight. Primary sensors, secondary sensors, and wearable devices capture plasma drug concentration, hydration status, Serum thyroglobulin, Acute Kidney Injury (AKI), and lifestyle factors such as sleep, activity, and dietary habits. Electronic health records furnish medical history, medication lists, and lab results. The system feeds this data into a predictive model, potentially a neural network like RNN or CNN, trained on a diverse dataset of patient responses to semaglutide. Algorithms like gradient boosting or reinforcement learning analyze the intricate interplay between semaglutide dose, Cmax concentration, dehydration risk, and blood sugar levels. The model undergoes rigorous training and validation for accuracy and to prevent overfitting. Utilizing the latest patient data, the model predicts Cmax, dehydration risk, and blood sugar response for potential semaglutide doses. A separate optimization algorithm, like a rule-based system, selects the optimal dose, minimizing the risk of exceeding Cmax threshold, dehydration, and maintaining normal blood sugar. This optimal dose is dynamically updated in real-time as patient data changes, ensuring dosing stays within regulatory guidelines using pre-defined safety limits. The system adjusts the final dose to be delivered by the implantable device based on the model's recommendations, leveraging them as valuable therapeutic input. Data privacy and security are rigorously maintained throughout the process. The model is continuously refined with new data and feedback from physicians and patients. Clinical trials and regulatory compliance processes guarantee safety and effectiveness for broader clinical application. This data-driven approach establishes a foundation for personalized semaglutide therapy, optimizing individual treatment while minimizing side effects and enhancing the patient experience.

An embodiment relates to a method comprising screening existing drug for potential new therapeutic indications using computational models, validating the computational predictions through laboratory experiments, developing an implantable device for the controlled delivery of the drug, and conducting clinical trials to confirm the efficacy of the drug in the new indication.

An embodiment relates to a method of clinical trial aid comprising monitoring and retrieving real-time health data of a subject via one or more sensors, storing the real-time health data in a first database, retrieving historical health data of the subject from a second database, delivering drug based on a personalized drug dosing regimen to body of the subject, enabling adjustment in the personalized drug dosing regimen by machine learning models, and wherein the method is configured for aiding in clinical trial. In some embodiments, the method further comprises retrieving local date and time from manual setting or cloud-based time to record drug dosing data. In some embodiments, the method further comprises monitoring said health data related to side effects and toxicity of delivered drugs. In some embodiments, the method further comprises automatically delivering drugs to the subject with authorization. In some embodiments, the method further comprises an interface for researchers to increase, decrease, pause or terminate dosing manually. In some embodiments, the method further comprises the machine learning model processing the real-time data, raising warning or pausing trial based on the analysis. In some embodiments, the method further comprises storing, making copies of and sharing retrieved and input data for research purposes.

An embodiment relates to a clinical trial aid system comprising an implantable device which is implanted inside body of a subject, one or more sensors configured to measure, retrieve and send the subject's real-time data of bioactivity and drug concentration, a data storage device configured to store censored, analyzed and manually input data, an input module for receiving censored and input health data, a machine learning model for processing and analyzing received data, an output module for presenting instructions, data and other necessary information, a drug dosing module delivering drugs under directions from one of the machine learning module and authenticated input instruction, and a data storage module for storing and backing up all data for further study use, wherein the system is configured to monitor and retrieve real-time health data of a subject via one or more sensors, store the real-time health data in a first database, retrieve historical health data of the subject from a second database, deliver drug based on a personalized drug dosing regimen to body of the subject, and enable adjustment in the personalized drug dosing regimen by the machine learning model. In some embodiments, the system further comprises a data processing module connected to the one or more sensors, wherein the data processing module receives digital signals from the one or more sensors and transfers signals to human-read and machine-read data. In some embodiments, the system further comprises a pre-trained AI model for processing and analyzing said health data and making predictions about side effects and toxicity of delivered drugs. In some embodiments, the system further comprises a user interface presenting health data, input prompts, predictions and reminders, wherein data types and layout of the interface can be manually set by users as needed.

Referring to FIG. 8, it shows clinical trial aid, according to one or more embodiments. "Clinical trial aid" refers to a system and method designed to support clinical trials by mechanisms such as monitoring subjects and collecting data from them to improve accuracy of the drug administration keeping in the mind ethical standards of the subjects. The system comprises an implantable device, an external monitoring platform, a data logging system, and a cloud-based analytics platform to enhance the precision and efficiency of clinical trials. The implantable device comprises an electronics module, further comprises a communication module and a control unit, and manages drug delivery and real-time data acquisition. The device operates using a power module that incorporates rechargeable batteries and energy-harvesting technology to ensure long-term functionality. Data from the device and one or more biosensors continuously streams to an external monitoring platform, which provides researchers and clinicians with live updates, alerts, and control options. The system logs all data securely through a data logging mechanism, leveraging blockchain technology to maintain accuracy and compliance. A cloud-based analytics platform processes this data, to optimize dosing regimens, predict adverse events, and analyze treatment responses. Machine learning algorithms like Logistic Regression, Random Forest, and Gradient Tree Boosting refine trial parameters and enhance decision-making. The system adapts dynamically to individual patient responses, enabling personalized treatment while identifying population-level trends and actionable insights. By integrating advanced drug delivery, real-time monitoring, and sophisticated analytics, the system supports adaptive clinical trials, accelerates drug development, and improves patient safety.

Referring to FIG. 9, it shows a flowchart for a clinical trial process via the implantable device, according to one or more embodiments. Step 902 of process 900 comprises safely implanting the device into recruited patients/participants under sterile conditions. The implantation process involves minimally invasive surgery performed in a sterile environment to reduce infection risk. Biocompatible materials ensure long-term safety, while anti-microbial coatings on the device further minimize infection risks. The implantation phase ensures a secure setup for the device. Algorithms such as Logistic Regression and Random Forest assist in patient selection by analyzing eligibility criteria based on clinical parameters, ensuring that only suitable candidates undergo the procedure. Post-implantation diagnostics confirm the device's functionality before patient discharge. Step 904 of the process 900 comprises configuring dosing regimens, frequency, and duration based on trial specifications. Once implanted, the device is programmed using software tailored to the clinical trial's requirements. This includes setting parameters for drug dose, delivery frequency, and duration. Algorithms within the device or linked systems enable precise customization, ensuring adherence to protocol-specific variables like individual pharmacokinetics (PK) and pharmacodynamics (PD). The term "Pharmacokinetics (PK)" refers to the study of how a drug is absorbed, distributed, metabolized, and eliminated by the body. Key parameters include Cmax, the maximum concentration of the drug in the bloodstream; Tmax, the time taken to reach this maximum concentration; and half-life, the time required for the drug's concentration in the bloodstream to reduce by half. These parameters are critical for understanding the drug's behavior in the body and optimizing dosing regimens to achieve therapeutic effectiveness while minimizing side effects.

The term "Pharmacodynamics (pd)" refers to the study of the effects of a drug on the body, including mechanisms of action and the relationship between drug concentration and its effect on the body of a user.

Advanced analytics, including Gradient Tree Boosting (GTB) and XGBoost, are used to analyze historical data and personalize initial dosing regimens. These algorithms consider patient demographics, disease pathology, and previous outcomes to set accurate delivery parameters. Step 906 of the process 900 comprises setting up a communication link between the implantable device and external monitoring platforms. The device is equipped with wireless communication modules (e.g., Bluetooth, Wi-Fi, or cellular connectivity) to transmit real-time data. Encrypted communication protocols ensure secure data transfer to cloud-based platforms or local monitoring systems, allowing remote access by researchers. Integration with IoT ecosystems further enables seamless connectivity across multiple devices and locations. Communication protocols leverage IoT frameworks, enabling seamless data transmission. Support Vector Machines (SVM) can classify real-time data flow anomalies, ensuring stable device-platform connectivity. Ensemble methods improve fault detection during this phase. Step 908 of the process 900 comprises administering the drug as programmed, using bolus dosing, continuous dosing, or dynamic dosing. The device supports multiple drug delivery modes such as bolus dosing, continuous dosing, and dynamic dosing. Bolus dosing delivers a rapid dose for acute conditions or therapeutic initiation. Continuous dosing maintains a steady drug concentration in the bloodstream or target site for chronic conditions. Dynamic dosing adjusts delivery rates in real-time based on patient response or detected biomarkers. Osmotically driven piston and motor actuated relief valve in the implanted device ensure accurate dosing in all modes. The device's microcontrollers execute dosing protocols using predefined instructions. Bayesian Causal Forest models optimize drug delivery modes by estimating heterogeneous treatment effects, ensuring individualized dosing for maximum efficacy and safety. Step 910 of the process 900 comprises tracking physiological parameters and drug efficacy through built-in sensors. Integrated biosensors monitor key physiological markers such as heart rate, temperature, and blood pressure, alongside drug-specific biomarkers like metabolite levels. These sensors provide real-time feedback on the patient's condition and the drug's impact. Advanced nanotechnology-based sensors allow high sensitivity and specificity in detecting molecular changes. Deep learning models analyze this multidimensional data, providing insights into the drug's real-time efficacy. Anomaly detection through Random Forest ensures that irregular patterns (e.g., signs of toxicity) are flagged immediately. Step 912 of the process 900 comprises streaming data to external monitoring platforms for immediate access by researchers. Data from the device is streamed continuously or at predefined intervals to secure monitoring platforms. Data transmission is managed through encrypted wireless channels. Naïve Bayesian Classifier algorithms ensure the secure classification of transmitted data based on relevance and urgency, allowing researchers to prioritize critical information. Cloud-based dashboards provide researchers with immediate access to metrics, trends, and alerts. This real-time data sharing improves decision-making and facilitates collaborative trial management across multiple sites. Step 914 of the process 900 comprises analyzing data on drug levels, patient vitals, and biomarkers to assess response. Data analysis software processes the transmitted data to evaluate drug efficacy and patient safety. Logistic Regression and Random Forest models predict patient outcomes by evaluating trends in biomarkers and vitals. Penalized Regression techniques are employed to identify subtle variations in response, particularly in heterogeneous populations. Advanced visualization tools present trends in drug levels, biomarker fluctuations, and patient vitals. Statistical and computational models help identify correlations between dosing regimens and therapeutic outcomes. Step 916 of the process 900 comprises Optimizing dosing using a machine learning platform. Machine learning algorithms analyze historical and real-time data to recommend dosing adjustments. Algorithms such as XGBoost and GTB refine dosing schedules dynamically, considering both real-time patient responses and historical data. This adaptive approach ensures precise delivery while minimizing risks of toxicity or underdosing. These models consider patient-specific variables, such as genetic predispositions, metabolic rates, and disease progression, to personalize treatment further. Continuous learning improves dosing accuracy as the trial progresses. Step 918 of the process 900 comprises predicting adverse events using the machine learning platform. Predictive analytics powered by AI identifies patterns in patient data that precede adverse events. Predictive models, including Causal Forest and Bayesian Causal Forest, assess heterogeneous treatment effects to anticipate adverse events. These models account for complex interdependencies among physiological parameters and drug effects, triggering preemptive alerts. Early warnings allow preemptive interventions, such as modifying dosing or halting drug delivery. Integration with historical clinical databases enhances prediction accuracy. Step 920 of the process 900 comprises modifying dosing schedules based on patient-specific responses. The system enables real-time modifications to dosing schedules using insights from biomarkers and patient vitals. Deep learning models analyze feedback from sensors to identify patterns indicating evolving conditions (e.g., developing tolerance or unexpected side effects). This data feeds into dosing algorithms to make real-time adjustments for personalized therapy. Automated feedback loops ensure timely adjustments to optimize therapeutic outcomes. For example, if a biomarker indicates insufficient drug levels, the device can increase the delivery rate. Step 922 of the process 900 comprises evaluating trial performance and deriving actionable insights. Data collected during the trial is aggregated and analyzed to evaluate performance metrics such as efficacy, safety, and adherence to protocols. Post-trial data is processed using Support Vector Machines (SVM) and Convolutional Neural Networks (CNN) to classify trial outcomes and identify success factors. Ensemble approaches aggregate results from multiple models, providing robust conclusions about drug efficacy and safety. Researchers can use this information to refine trial designs, identify patient subgroups with favorable responses, and make informed decisions about the drug's future development. Step 924 of the process 900 comprises continuously recording all delivery and response data for accuracy. The system maintains a comprehensive log of all drug deliveries, patient responses, and sensor data. In some embodiments, data logging systems may utilize blockchain technology for secure, immutable records. Gradient Tree Boosting (GTB) ensures that critical trends in patient responses are logged and highlighted for future reference. In some embodiments, machine learning models will aid in refining trial protocols for subsequent phases. The system transforms clinical trials into highly controlled, adaptive, and efficient processes, ensuring better outcomes for patients and researchers.

An embodiment relates to a method comprising identifying a drug that has compatibility with an implantable device, reformulating the drug to enhance at least one of a stability and solubility, loading the drug into the implantable device to form a drug-device combination, implanting the drug-device combination into a subject, releasing the drug in a controlled manner via the drug-device combination into body of the subject, monitoring an effect of the drug in the body of the subject, and accessing safety, tolerability, and pharmacokinetics of the drug in the body of the subject.

An embodiment relates to a method comprising identifying a drug that has stability, solubility and compatibility with an implantable device, loading the drug into the implantable device to form a drug-device combination, implanting the drug-device combination into a subject, releasing the drug in a controlled manner via the drug-device combination into body of the subject, monitoring an effect of the drug in the body of the subject, and accessing safety, tolerability, and pharmacokinetics of the drug in the body of the subject. The drug does not cause adverse reactions when in contact with the device and surrounding tissues and the implantable device safely delivers the drug over a prolonged period. In some embodiments, the method further comprises monitoring the drug-device combination for long-term safety and efficacy. In some embodiments, the method further comprises providing an alarm on occurrence of an adverse effect of at least one of the drug and the implantable device. In some embodiments, the method further comprises providing an alarm on occurrence of an error in release of the drug.

Referring to FIG. 10, it shows a process for drug repurposing via the system, according to one or more embodiments. The process of drug repurposing using the implantable drug delivery device begins with selecting a candidate drug and preparing it in a formulation suitable for the device, ensuring compatibility and effectiveness. The device is implanted under sterile conditions, with precise placement to enable targeted delivery. Researchers configure the device with trial-specific dosing parameters, such as dose amount, frequency, and duration. The device administers the drug in bolus, continuous, or dynamic modes, adjusting delivery in real-time based on feedback from integrated biosensors. These sensors monitor physiological parameters and biomarkers, ensuring accurate assessment of the drug's efficacy and safety. The device wirelessly transmits collected data to an external monitoring platform, which displays real-time trends and flags anomalies. A cloud-based analytics platform processes this data, applying machine learning models to optimize dosing regimens, predict adverse events, and analyze treatment outcomes. The system continuously adapts dosing schedules based on patient-specific responses, creating a dynamic feedback loop that enhances the precision of the repurposing process. As the trial progresses, researchers synthesize comprehensive data to evaluate the drug's effectiveness for its new therapeutic indication. This approach supports adaptive, precise, and efficient trials, reducing systemic side effects and accelerating the drug development timeline.

The system for aiding in drug repurposing leverages one or more advanced algorithms to support the complex and dynamic process of drug repurposing. Matrix Factorization techniques can be employed to rank broad-spectrum antivirals by identifying potential candidates with the highest likelihood of efficacy across multiple conditions. Graph-based algorithms, such as graph kernels, rank drugs by analyzing network perturbations, while tools like Graph-SAGE and HinSAGE generate low-dimensional vector representations of molecular interactions to reveal novel drug-target associations. Machine learning methods, including the Iterative Stochastic Elimination (ISE) algorithm, create ligand-based models for precise drug targeting, and Multimodal Restricted Boltzmann Machines (MM-RBM) combine data from diverse sources to improve prediction accuracy. Deep learning approaches, particularly pre-trained models, will facilitate embedding generation and enable transfer learning to accelerate drug discovery for new indications. Network analysis techniques, such as Heterogeneous Graph Attention Networks (HGNA) and Graph Convolutional Networks (GCN), may provide powerful tools for analyzing complex relationships in pharmacological and clinical datasets. Bayesian methods, like Bayesian Network Meta-Analysis (NMA), predict treatment efficacy by synthesizing data from multiple trials, offering probabilistic insights into drug performance. Tensor Factorization, including Tensor-Matrix-Tensor (TMT) methods with gradient-based factorization, identifies latent patterns in multidimensional trial data, while Association Rule Mining combines If-Then rules with discrete optimization to uncover hidden drug-disease relationships. By integrating one or more of these algorithms, the system can analyze vast and diverse datasets from the implantable device and external platforms, enabling precise patient selection, dynamic dosing adjustments, and accurate prediction of adverse events. These computational tools will enhance the overall process, driving faster and more reliable repurposing of drugs with reduced trial costs and improved safety profiles.

If a drug is being delivered through an implantable device, positioned remotely from where the drug is needed, it would be useful to efficiently deliver the drug to a remote location without dilution. It is worth noting that peptide receptor radionuclide therapy (PRRT) is a type of internal radiotherapy, which is chemically targeted, but not always locationally. It has been used as a treatment for neuroendocrine tumors that cannot be easily removed. It would therefore be useful to deliver drugs to tumors and other locations without delivering it to non-tumorous regions.

In an embodiment, a catheter-like tube is provided that is fixed, or removably attached, to the implantable device to deliver a drug anywhere in the body. This would be helpful if the target delivery region is far from a location where the implantable device is located, especially if the delivery should be focused on a particular sub-cutaneous region, including deep within the body, such as a tumor.

The catheter-like tube could take any form. For example, in some embodiments, it will have a secure connector at one end for connecting to the implantable device. The secure connector will permanently attach the tube to the implantable device. If permanently attached, the implantable device will be configured to make the tube and the device integral with one another. Alternatively, the connector will be used to temporarily attach the tube to the implantable device, which would allow the tube to be reusable. If the device is temporarily attached, the implantable device should be easy to attach and detach to the tube, permitting the tube to be reusable with minimal leakage and insignificant risk of infection. As with many catheter insertion methods, slightly invasive surgery may be required to position the tube correctly. Before, after, or during insertion of the tube, the implantable device would be inserted using any suitable technique. The tube would connect to the drug reservoir of the implantable device, which is typically located subcutaneously (e.g., in the forearm). In case the drug reservoir is small, it may need to be replaced periodically, so a secure connector will be used to easily replace the reservoir periodically. The newly replaced implantable device can be customized to deliver a different drug over time, as deemed necessary for optimal therapeutic efficacy. In fact, a series of devices can be used over time to change the drug profile slowly or more rapidly, if needed. The use of a tube will also minimize the amount of drug needed to treat a highly localized region because the drug is delivered directly to where it is needed. In some ways, this is like external beam radiation therapy, which narrowly targets areas of interest in the body while minimizing the broader negative side effects of radiation to the body. In some embodiments, the tube will be oriented in such a way as to permit the connector (the proximate end of the tube) to be easily removed from the body while maintaining the position tube outlet or tip (distal end of the tube) to remain relatively stationary. One way is to add a flexible loop along the length of the tube, which would minimize the force felt at the distal end when the proximate end is being moved or reattached inside or outside the body. At the drug delivery end, the tube can take shapes and sizes that are customized for any particular use case.

In one embodiment, a drug of any kind (such as a cancer radiation drug) is delivered through the tube to any specific region (e.g., cancerous region, such as the lung, the spleen, the prostate, the heart, etc.).

A benefit of this targeted drug delivery approach is that it is fast and easy to implant the tube to deliver a drug to a targeted region of the body, and even to replace the implantable device while keeping the catheter in place. Another benefit is that a patient need not participate in expensive and remote external beam radiation therapy sessions, although they could be performed in combination with the targeted drug delivery approach.

Referring to FIG. 11A, it illustrates an implantable device 1100 comprising a semi-permeable membrane plug 1102, a compressible piston 1104, and a catheter 1170, wherein the catheter 1170 is attached to the drug delivery outlet 1114 of the implantable device 1100 by sleeving a catheter sleeve 1172 over the drug delivery outlet. The drug delivery outlet 1114 of the implantable device 1100 comprises a flow channel 1175 that fluidically connects the catheter 1170 with the implantable device 1100.

Figure 11B:
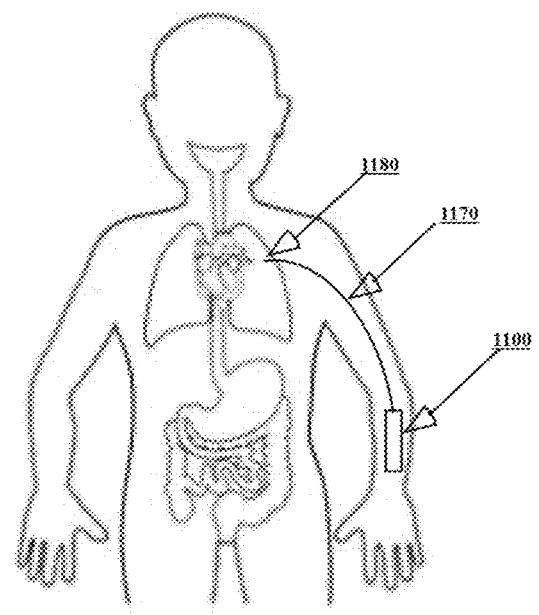
FIG. 11B depicts the delivery of a drug to a target organ via the implantable device through a catheter, according to one or more embodiments.

Referring to FIG. 11B, it depicts the delivery of a drug to a target organ (heart) via the implantable device 1100 through an outlet 1180 of a catheter tube 1170.

Figure 11C:
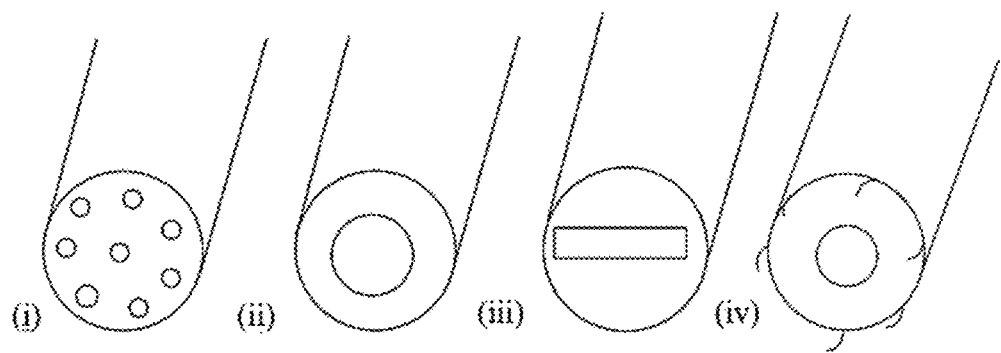
FIG. 11C shows example embodiments of a drug-releasing end of a catheter.

Referring to FIG. 11C, it shows exemplary drug-releasing end of a catheter, according to one or more embodiments. In (i) of FIG. 11C, the catheter tube 1170 comprises a "mist" outlet to cover and shower a tumor. In (ii) of FIG. 11C, the catheter tube 1170 comprises a "jet" outlet to precisely release the drug onto the tumor. In (iii) of FIG. 11C, the catheter tube 1170 comprises a "rectangular opening" outlet to precisely release the drug onto the tumor. In (iv) of FIG. 11C, the catheter tube 1170 comprises an outlet with one or more hooks to attach directly to the tumor, ensuring no movement will shift the placement of the catheter tube 1170.

Figure 11D:
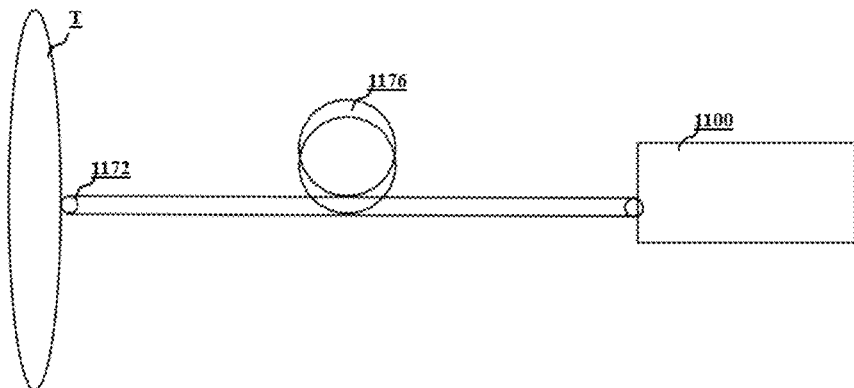
FIG. 11D illustrates an implantable device comprising a catheter, according to one or more embodiments.

Referring to FIG. 11D, it illustrates an implantable device 1100 comprising a catheter, according to one or more embodiments. The catheter tube 1172 comprises a loop 1176, connecting the implantable device 1100 with the tumor T, to provide slack without creating tension on the tumor.

In an embodiment, the drug delivery portion of the implantable device 1100 and the outlet of the catheter tube comprise magnets to establish a fixed connection. The magnets align to provide a secure connection.

Figure 11E:
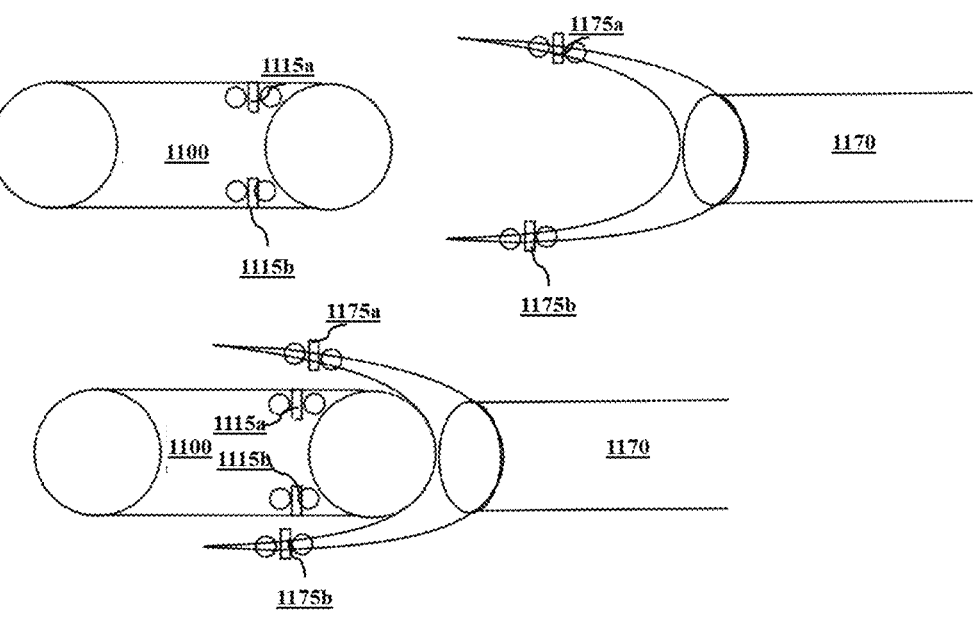
FIG. 11E shows a schematic of attaching the implantable device to a catheter using magnets, according to one or more embodiments.

Referring to FIG. 11E, it shows a schematic of attaching the implantable device 1100 to a catheter using magnets, according to one or more embodiments. The circular exit port of the implantable device 1100 comprises one or more magnets (shown as rectangles 1115a and 1115b). One end of the catheter tube 1170 also comprises a structure comprising magnets (shown as rectangles 1175a and 1175b). The magnets ensure a tight seal between the catheter tube 1170 and the implantable device 1100.

Figure 11F:
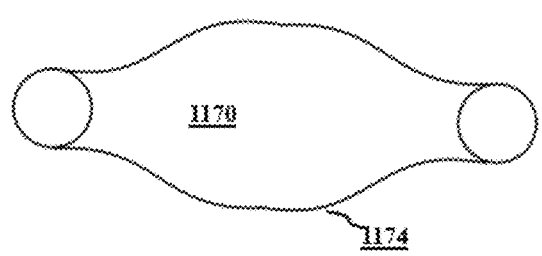
FIG. 11F shows a catheter comprising a tube comprising a "balloon" portion, according to one or more embodiments.

In some embodiments, a catheter "balloon" may also be used to increase the amount of drug for sustained drug delivery. Referring to FIG. 11F, it shows a catheter tube 1170 comprising a "balloon" portion 1174, according to one or more embodiments. The balloon portion along the catheter tube is configured to increase its capacity of reservoir and to provide additional axial flexibility.

Figure 12:
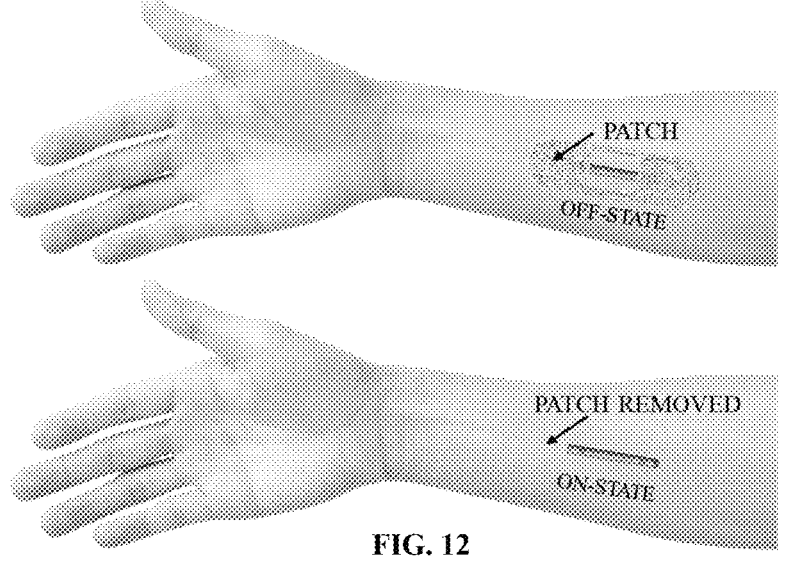
FIG. 12 depicts prevention of accidental release via a non-conductive patch on the skin over the implantable device via a patch, according to one or more embodiments.

Referring to FIG. 12, it depicts prevention of accidental release via a non-conductive patch on the skin over the implantable device, according to one or more embodiments. The implantable device will be implanted in a human body non-surgically in a doctor's office. The drug will be delivered via a touch sensor incorporated within the device utilizing a non-radiative near-field communication technology such as the Wi-R technology.

Wi-R technology, with its unique utilization of Electro-Quasistatic (EQS) fields, presents a novel approach to touch-based activation of devices. Touch-based activation harnesses the power of EQS fields to provide a secure, efficient, and user-friendly interface for a wide range of devices. By detecting and responding to touch, devices can offer enhanced security and convenience, making Wi-R an innovative solution in the realm of wireless communication and device interaction.

Touch-based activation using Wi-R technology leverages the proximity and interaction of a human touch to create a secure and efficient communication channel between a user and the device. This interaction can initiate the activation process by triggering a series of events within the device.

The device generates an EQS field around its surface. This field is sensitive to changes in its immediate environment, particularly those caused by the proximity of a human hand or finger. When a user's hand approaches the device, the EQS field is disturbed. The device's sensors detect these disturbances, identifying the presence of a potential user touch. The device analyzes the characteristics of the disturbance in the EQS field to confirm it is a deliberate touch. This helps differentiate between accidental brushes and intentional activations. For enhanced security, the device can incorporate additional authentication mechanisms. For example, it might analyze the unique electrical properties of the user's skin or require a specific touch pattern to activate. Upon confirming a valid touch, the device initiates its activation sequence. This could involve powering up the device, unlocking user interfaces, or starting specific applications.

Wi-R technology's energy-efficient nature ensures that the touch detection and activation process consume minimal power, making it suitable for battery-powered devices. The device can provide immediate feedback to the user through visual, auditory, or haptic signals, indicating that the touch has been recognized and the device is activated.

The confined nature of the EQS field ensures that the activation signal remains within a very close range, reducing the risk of unauthorized access. The ultra-low energy consumption of Wi-R technology makes it ideal for devices that rely on battery power, ensuring long-lasting operation. Touch-based activation provides a seamless and intuitive way for users to interact with their devices, eliminating the need for buttons or other physical interfaces. This technology can be applied to a wide range of devices, from wearables and smartphones to smart home devices and medical equipment.

In some embodiments, the triggering is done via a sensor integrated to the device, wherein the sensor is operable to detect a presence of opioid in the subject's body.

In an embodiment, the implantable device is a single-use implantable device with a biosensor. In another embodiment, the implantable device will be a multiple use device to deliver multiple doses of Naloxone with built-in biosensor for opioids. The device could significantly reduce the number of opioid-related deaths by providing a timely and effective response to overdoses. By blocking the effects of opioids in the body and restoring normal breathing, Naloxone can prevent death following an opioid overdose. The use of an implantable device ensures that Naloxone is readily available when needed, potentially saving thousands of lives each year. Furthermore, this solution could alleviate the economic burden of the opioid crisis by reducing healthcare and criminal justice costs associated with opioid overdoses.

In an embodiment, the device comprises a biosensor: The biosensors provide real-time monitoring of drug levels and/or health related markers, offering valuable insights for personalized treatment for triggering either the skin touch or the integrated sensor device.

In an embodiment, the implantable device is a one-time use on-demand tubular implantable device of size 4 mm diameter and 6-8 cm length containing a Naloxone dose adjusted to the subject's weight. The implantable device will be implanted in a human body non-surgically in a doctor's office. In the implantable device for Naloxone delivery, the drug will be delivered via a touch sensor incorporated within the device utilizing a non-radiative near-field communication technology such as the Wi-R technology of IXANA®. While "Naloxone has virtually no effect in people who have not taken opioids", to prevent accidental release, the person wears a non-conductive patch on the skin over the implantable device. When the release of Naloxone is necessary, the person or observer peels off the non-conductive patch and touches the skin directly over the implantable device. This touch triggers the release of Naloxone. The non-conductive patch would state in bold, "PEEL THE PATCH AND TOUCH THE SKIN BELOW THE PATCH IF THE PERSON WEARING THE PATCH IS EXPERIENCING OPIOID OVERDOSE."

An embodiment relates to a system comprising an implantable device, a patch and an emergency caller wearable. The patch and implantable device are integrated with the emergency caller wearable (example: pendant type 911 caller). Someone going through overdose can activate the 911 calling pendant, which in turn activates the patch, which in turn activates the implantable device.

Figure 13:
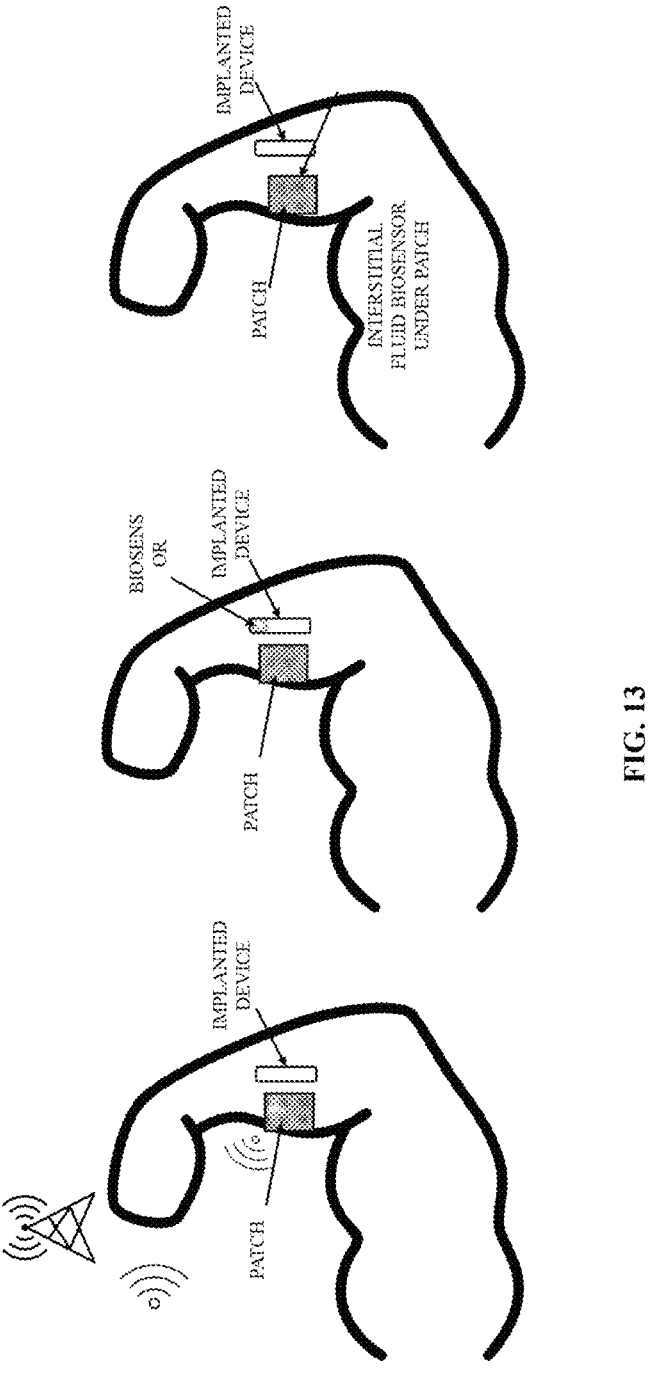
FIG. 13 shows the schematics of an arm with a smart patch on top of an implantable device, according to one or more embodiments.

Referring to FIG. 13, it shows a schematic of a system comprising a smart patch, an implantable device, according to one or more embodiments.

In an embodiment, the system further comprises a biosensor coupled to the microcontroller to verify a medical characteristic of the patient prior to delivery of the opioid, the opioid agonist or the partial opioid agonist, wherein the biosensor comprises a pulse oximeter, a heart rate sensor, an ECG sensor, a skin sensor, a temperature sensor, and/or a blood flow sensor.

Referring to FIG. 14 shows a schematic of an automated overdose response system comprising an emergency alert device (Example: wearable emergency calling device), a smart patch and an implantable device, according to one or more embodiments. The emergency alert device can be activated either manually by the user or automatically by a biosensor detecting an overdose. Once triggered, it sends an emergency alert to 911, notifying emergency services of the situation. Additionally, it can signal the smart patch to release medication. The smart patch is equipped with a biosensor that monitors the user's physiological parameters. Upon detecting signs of an overdose, the biosensor sends a signal to the patch to initiate drug release. The patch can also be triggered by the emergency alert device to release naloxone, a medication used to counteract opioid overdoses. The implantable drug delivery device is implanted in the user's body and contains a reservoir of naloxone. It is designed to rapidly deliver the medication in response to signals from either the smart patch or the emergency alert device. This ensures that the user receives the life-saving drug as quickly as possible during an overdose. The biosensor in the smart patch continuously monitors the user's vital signs. If it detects an overdose, it sends a signal to both the emergency alert device and the implantable drug delivery device. The emergency alert device then calls 911, providing emergency services with the user's location and details of the overdose. Simultaneously, the smart patch or the emergency alert device triggers the implantable drug delivery device to release naloxone. This rapid response is crucial in reversing the effects of the overdose and stabilizing the user until help arrives. This integrated system ensures a swift and coordinated response to an overdose, significantly increasing the chances of survival and recovery.

In an embodiment, the system is configured with a software to control working of the system. The biosensor comprises a blood pressure sensor, a temperature sensor, and a heart rate sensor, a tactile sensor, and wherein the non-bio-sensor comprises a BLE sensor.

In an embodiment, the release of the drug starts on a signal, wherein the signal is regulated manually comprising a release button or automatically based on physiological condition of a user.

In an embodiment, the software sends an alert to a user on a working condition of the patch, wherein the working condition includes an overdose of the drug, an accidental loss of the patch, a defunct power source, an empty cartridge or any combination thereof.

In an embodiment, the device is integrated with a mobile app for real-time monitoring and adjustments. In some embodiments, the device is configured to automatically shut-off in case of pressure anomalies. In some embodiments, the device comprises a rechargeable battery to ensure long-term use without frequent replacements.

An embodiment relates to a machine learning model that can detect drug overdosing via a biosensor by integrating multiple vital signs such as oxygen saturation, respiration rate, and motion into a single capsule network-based machine learning model. The model is designed to be used with wearable devices, making it more accessible and practical for real-time monitoring and intervention.

FIG. 15 outlines steps for evaluating drug overdose using vital-signs evaluation with machine learning, from data collection and preprocessing to model development, deployment, and alert generation. In the process of evaluating drug overdose using vital-signs evaluation with machine learning, Step 1502 comprises data collection using at least one of a wearable device, patch, or drug delivery device. Step 1504 comprises data preprocessing. In Step 1506, feature extraction is performed on the collected data. Step 1508 comprises model development using a machine learning algorithm. Step 1510 comprises severity classification based on extracted features and human input to re-develop, refine, and train the model. Step 1512 comprises model evaluation. In Step 1514, the model is deployed to at least one of the wearable device, the patch, or the drug delivery device. Step 1516 comprises drug dosing via the implantable device. Step 1518 comprises alert generation via at least one of the wearable device and the patch.

FIG. 16 outlines a process of evaluating drug overdose using vital-signs evaluation with machine learning. Step 1602 comprises collecting data from at least one of a wearable device, a patch comprising a biosensor, or an implantable device comprising a biosensor. Step 1604 focuses on monitoring one or more vital signs, comprising oxygen saturation (SpO2), respiration rate, motion, skin tone, body physiology, and photoplethysmography (PPG) signals. Step 1606 entails cleaning and preprocessing the collected data, while Step 1608 addresses handling missing values and noise in the data. In Step 1610, relevant features are extracted from the raw data. Step 1612 comprises developing a capsule network-based machine learning model, known as OxyCaps. Step 1614 is dedicated to training the model using data from patients with a reference surrogate data, such as sleep apnea, for opioid overdose data. Step 1616 classifies the severity of hypoxemia into multiple severity levels, for example, Normal (96%-100%), Moderate (92%-95%), and Severe (91%-88%). Step 1618 evaluates the model's performance, and Step 1620 measures accuracy, recall, and other relevant metrics. In Step 1622, the model is deployed in at least one of the wearable devices, the patch, or the implantable device. Step 1624 comprises monitoring real-time vital signs and detecting potential overdoses. Finally, Step 1626 comprises injecting the antidote drug via the implantable device. Step 1628 comprises implementing an alert system to notify emergency responders in case of a detected overdose.

Figure 17:
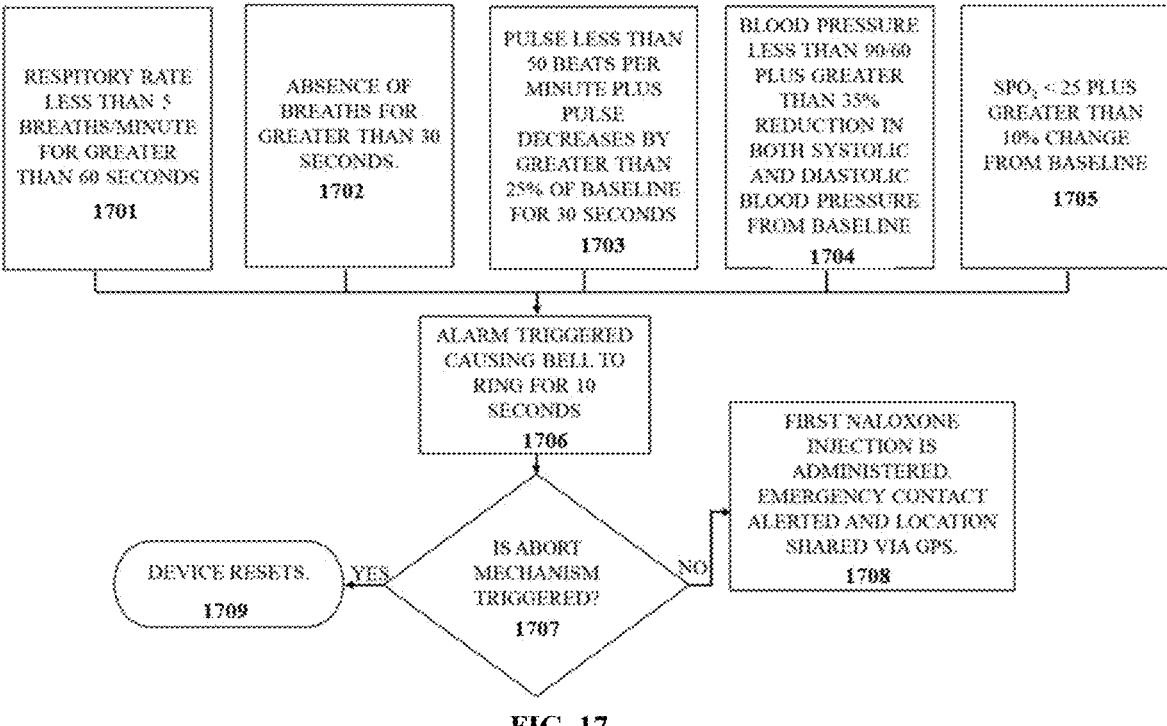
FIG. 17 is an exemplary flow chart showing the methodology for detection of an opioid overdose described in the present disclosure. The flow chart includes steps for activation of an actuator for administration of naloxone.

FIG. 17 is an exemplary flow chart showing the methodology for detection of an opioid overdose and activation of an actuator for administration of an antidote to the opiate. Should any one of the criteria in the top row of FIG. 17 occur, the process of impending opioid receptor antagonist administration and overdose reversal begins. Significant decrease in respirations 1701, 1702, pulse 1703, blood pressure 1704, or peripheral capillary oxygen saturation (SpO2) 1705 are all physiological signs that may be present during an overdose and will trigger this process. Not all of these conditions must be met to trigger the overdose and any one of 1701, 1702, 1703, 1704, and 1705 individually may be sufficient to activate the opioid receptor antagonist injection. Also, should more than one occur at once or if all conditions are met simultaneously, the process of impending opioid receptor antagonist administration will be triggered.

As noted in FIG. 17, once a criterion has been met, and the device recognizes an overdose, then an alarm within patch is triggered 1706. This happens prior to the administration of the opioid receptor antagonist and gives the individual time to abort the injection 1707 in the unlikely event of an error. If the individual is conscious (or becomes conscious from a sleeping state) and aborts the injection then the implantable device resets 1709 thereby no release of the opioid antedote. It then resumes monitoring for any further signs of overdose as noted in 1701, 1702, 1703, 1704, and 1705 and begins the cascade should one of them occur again.

In the unlikely event of three abortions within 30 minutes, the device resets for 6 hours permitting the individual to seek medical treatment or assistance to determine the issue and avoid unnecessary disruptions or unnecessary naloxone administration due to a faulty device, medical condition that could mimic overdose, or other reason. Additionally, an individual not using opioids who experienced a false positive would know that overdose was not a factor, and so that individual may consider placing the device into the "reading mode" in attempt to establish a new baseline and improve accuracy of the device.

If the abort mechanism 1707 is not triggered within a short time period, for example, 20 seconds or at all, then as the algorithm demonstrates, opioid receptor antagonist shall be administered 1708 from the implantable device. Patch connects to a device for emergency contact, e.g., emergency calling device is activated, and GPS coordinates of the location provided to the contact.

Drug formulation within the drug chamber contains sufficient opioid receptor antagonist, e.g., naloxone to reverse a typical opioid overdose. In certain embodiments the dosage may be 0.4 mg naloxone. Given that the locations the device administers the opioid receptor antagonist includes those (body locations) that have not previously been used to reverse an overdose (the wrist or ankle for example), it should be understood that a different dose may be optimal for these locations and it may be greater or less than 0.4 mg.

The device may be equipped to record the preceding 5 or 10 minutes prior to and after the administration of opioid receptor antagonist in order to promote future research and improvement regarding this algorithm. While each individual criterion 1701, 1702, 1703, 1704, 1705 is sufficient to begin to reversal process, less or more strict criteria may prove more useful, and may be used. By combining parameters such as SpO2, low blood pressure and low pulse or low respiratory rate, and requiring that they all be satisfied, the likelihood of false alarms goes down, though the risk of a missed overdose may increase. With regard to monitoring blood pressure, through the use of pulse transit time, an accurate analysis of systolic, diastolic, and mean arterial pressure can be obtained and used in determining whether an overdose has occurred.

In some embodiments, the system further comprises a geofencing feature integrated within the analytics platform and communication unit. Geofencing refers to the ability of the system to define virtual geographical boundaries and monitor the location of the implanted device or external sensors. The geofencing features location-based alerts and sends notifications when the patient moves outside predefined safe zones or enters restricted areas that could impact treatment or device functionality (e.g., areas with high electromagnetic interference). In some embodiments, the system can customize dosing based on location and adjust drug delivery regimens dynamically based on environmental factors associated with specific locations, such as altitude or temperature changes that could influence physiological responses. In some embodiments, the system provides additional safeguards by tracking the location of the device and ensuring it remains within approved zones, reducing risks of misuse or unauthorized operation.

Figure 18:
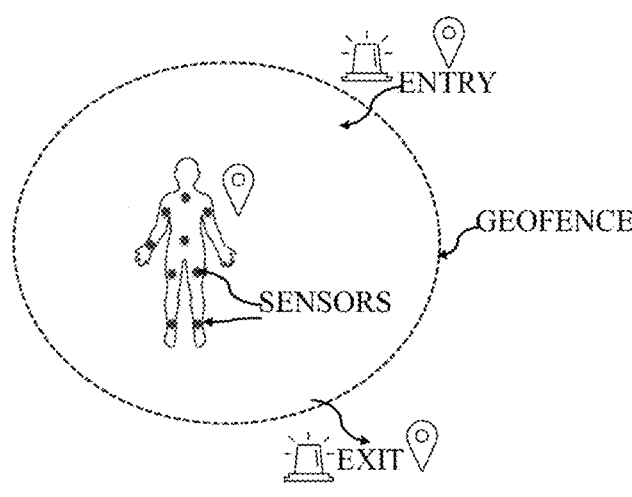
FIG. 18 shows use of geofencing for substance abuse prevention, according to one or more embodiments.

Referring to FIG. 18, it shows the use of geofencing for substance abuse prevention, according to one or more embodiments. Geofencing can create virtual boundaries around Global Positioning Systems (GPS) coordinates in order to detect a user's presence in a specific area of interest, e.g., bars, clubs, liquor stores; and GPS tracking allows for real-time study of user behavior, as well as enhanced ability to influence it.

Figure 19A:
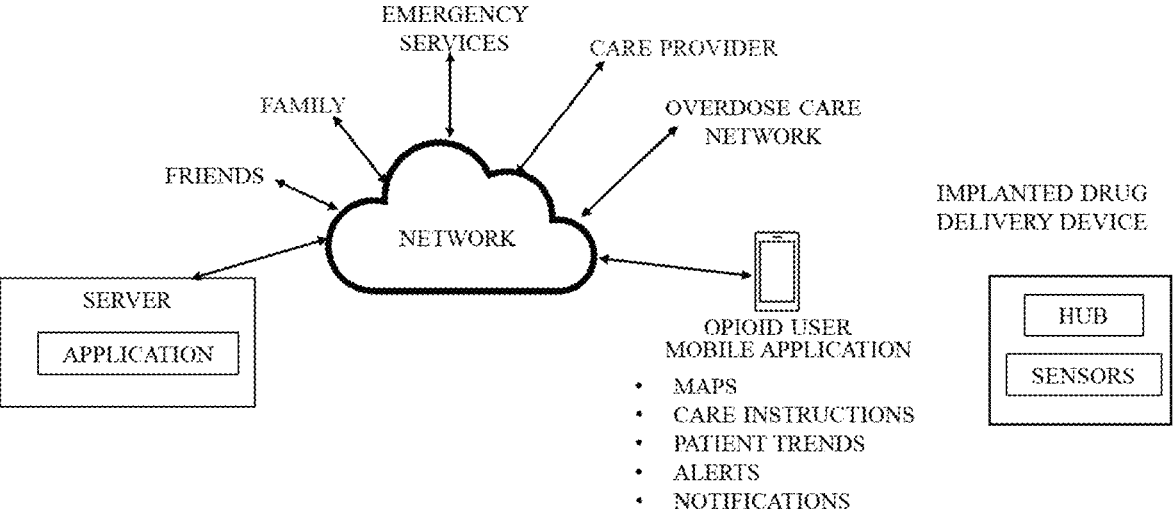
FIG. 19A is an overview of an example communication network initiated via the system.

In an embodiment, the system comprises opioid use monitoring and notification component. Referring to FIG. 19A, it provides an overview of an example communication network initiated via the system. The opioid users' support network can include friends, family, emergency services, care providers, and overdose care networks, for example, that communicate over a network, such as the Internet. The support network receives notifications and/or status updates of the opioid user's condition. An optional monitoring device can monitor the opioid user's respiration and other biological parameters, such as heart rate, blood oxygen saturation, perfusion index, for example, and provides the parameters to the smart device. An application running on the smart device can determine whether an opioid overdose event is imminent and/or occurring. The application can also provide additional information, such as care instructions, patient trends, medical opioid information, care instruction, user location, the location of naloxone, buprenorphine, buprenorphine in combination with naloxone, or other medication used to reverse the effects of an opioid overdose, and the like. The support network, after receiving a notification, can communicate with a central server to obtain the additional information.

Figure 19B:
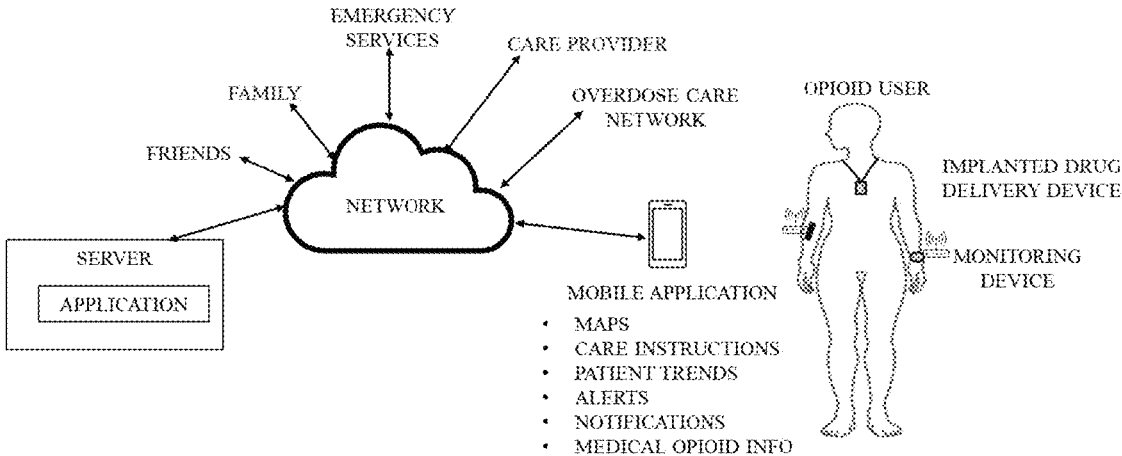
FIG. 19B is another overview of a communication network initiated via the system.

Referring to FIG. 19B, it provides an overview of another example of communication network via the system. As illustrated above in FIG. 19A, the opioid users' support network can include friends, family, emergency services, care providers, and overdose care networks, for example, that communicate over a network, such as the Internet. The support network receives notifications and/or status updates of the opioid user's condition. A monitoring device including a sensor can monitor the opioid user's respiration and other biological parameters, such as heart rate, blood oxygen saturation, perfusion index, for example, and provide the parameters to a HUB device that can communicate over the network. An example of a HUB device is illustrated in FIG. 19B. The HUB device receives the sensor data from the sensor. The HUB device can send the sensor data over the network to the server. The HUB device can at least partially process the sensor data and send that sensor data to the server. The server processes the sensor data, or the at least partially processed sensor data, and determines whether an overdose event is imminent and/or occurring. When an overdose event is imminent and/or occurring, the server notifies the support network and the mobile application on the opioid user's mobile device.

It should be noted that the flowchart and the suggested time limits and parameters are meant to be exemplary, and that there could be other measures or criteria used in order to maximize safety and accuracy.

What is claimed is:

1. A system for a personalized drug dosing, comprising:
(a) an implantable drug delivery device comprising:
(i) a drug reservoir configured to store a drug;
(ii) a pump configured to deliver the drug from the drug reservoir into a body of a mammal according to a drug dosing regimen; and
(iii) an electronic module comprising a chip configured to control operation of the pump;
(b) one or more physiological sensors configured to generate physiological data in real-time from the body of the mammal;
(c) an analytics platform comprising:
(i) an input module configured to receive the physiological data from the one or more physiological sensors; and
(ii) an output module configured to transmit information to the implantable drug delivery device; and
(d) a feedback control system comprising the electronic module, the one or more physiological sensors, and the analytics platform;
wherein the feedback control system is configured to:
(i) receive the physiological data from the one or more physiological sensors;
(ii) analyze the physiological data to determine a therapeutic effectiveness indicative of a therapeutic effect of the drug;
(iii) generate a dosing adjustment based on the therapeutic effectiveness; and
(iv) transmit the dosing adjustment to the electronic module of the implantable drug delivery device to modify the drug dosing regimen implemented by the pump.

2. The system of claim 1, further comprising a database, wherein the database includes drug effect information corresponding to the drug stored in the drug reservoir, and wherein the database is configured to be updated with real-world data collected from multiple users administered the drug.

3. The system of claim 2, wherein the analytics platform is configured to perform bidirectional data communication, the input module of the analytics platform being configured to receive data from at least one of: (i) the database, (ii) the one or more physiological sensors, and (iii) the implantable drug delivery device, and the output module being configured to transmit processed data to the implantable drug delivery device.

4. The system of claim 3, wherein the bidirectional data communication includes transmitting an alert signal in real-time.

5. The system of claim 2, wherein the analytics platform is configured to execute one or more machine learning models, artificial intelligence (AI) based prediction models, or adaptive algorithms for processing the real-world data stored in the database.

6. The system of claim 1, wherein the analytics platform comprises a pharmacokinetic/pharmacodynamic (PK/PD) modeling module configured to predict a therapeutic response to the drug in the body of the mammal.

7. The system of claim 1, further comprising a mobile application configured to present healthcare providers with interpretive outputs or recommendations relating to the drug dosing regimen.

8. The system of claim 1, further comprising a patient preference module configured to capture and integrate patient-specific preferences regarding therapeutic efficacy and safety trade-offs for the drug, wherein the analytics platform uses patient-specific preferences to personalize the drug dosing regimen.

9. A method for a personalized drug dosing, comprising:
(a) monitoring physiological data related to a drug in real-time using one or more physiological sensors positioned to collect data from a mammal;
(b) collecting and transmitting the physiological data in real-time to an analytics platform; and
(c) implementing a feedback control process comprising:
(i) receiving the physiological data at the analytics platform;
(ii) analyzing the physiological data to generate a therapeutic effectiveness indicative of a therapeutic response to the drug;
(iii) generating a dosing adjustment based on the therapeutic effectiveness;
(iv) transmitting the dosing adjustment to an implantable drug delivery device comprising a pump; and
(v) updating a drug dosing regimen executed by the pump based on the dosing adjustment parameter.

10. The method of claim 9, further comprising configuring the implantable drug delivery device with drug-related data, the drug-related data comprising at least one of: (i) a drug identifier specifying a type of drug contained in the implantable drug delivery device, (ii) an initial dosage range for the drug, and (iii) one or more delivery parameters controlling dosing of the drug.

11. The method of claim 10, further comprising integrating, within the analytics platform, historical patient data with the drug-related data and the physiological data for the mammal.

12. The method of claim 9, further comprising calibrating the one or more physiological sensors to optimize monitoring of the physiological data.

13. The method of claim 9, further comprising generating and transmitting an alert signal in real-time upon detecting a predicted adverse event.

14. The method of claim 9, further comprising generating a treatment progress report summarizing patient response and therapeutic effectiveness over time.

15. The method of claim 9, further comprising updating one or more algorithms executed by the analytics platform based on new physiological data, patient outcomes, or clinician input.

16. The method of claim 9, further comprising:
(a) receiving pharmacokinetic data for the drug from a first database;

(b) receiving side-effect data for the drug, including information regarding adverse effects and toxic concentration thresholds, from a second database;

(c) training a machine learning model to predict a minimum effective drug concentration associated with minimal side effects in the body of the mammal implanted with the implantable drug delivery device; and (d) generating the drug dosing regimen based on an output of a trained machine learning model.

17. The method of claim 16, further comprising acquiring a measured concentration of the drug in plasma or serum of the mammal.

18. The method of claim 16, further comprising acquiring a measured biomarker concentration or a disease-associated vital sign affected by the drug.

19. The method of claim 16, further comprising retraining the machine learning model using a received pharmacokinetic data and side-effect data to improve accuracy of a predicted minimum effective drug concentration associated with minimal side effects.

20. The method of claim 16, wherein the pharmacokinetic data comprises at least one of: drug clearance rate, volume of distribution, drug half-life, bioavailability, maximum plasma or serum concentration (Cmax), and time to achieve Cmax (Tmax).

* * * * *